US009028529B2

(12) United States Patent
Fox et al.

(10) Patent No.: US 9,028,529 B2
(45) Date of Patent: May 12, 2015

(54) SYSTEMS AND METHODS FOR CLOSING A TISSUE OPENING

(75) Inventors: Andrew D. Fox, Westborough, MA (US); Daniel J. Riskin, Los Angeles, CA (US); Michael Barenboym, Framingham, MA (US)

(73) Assignee: DermaClip US, LLC, Houston, TX (US)

( * ) Notice: Subject to any disclaimer, the term of this patent is extended or adjusted under 35 U.S.C. 154(b) by 0 days.

(21) Appl. No.: 13/447,815

(22) Filed: Apr. 16, 2012

(65) Prior Publication Data

US 2012/0203273 A1 Aug. 9, 2012

Related U.S. Application Data

(63) Continuation of application No. 12/059,485, filed on Mar. 31, 2008, now Pat. No. 8,157,839, which is a continuation-in-part of application No. 11/217,127, filed on Aug. 31, 2005, now abandoned.

(Continued)

(51) Int. Cl.
*A61B 17/08* (2006.01)
*A61B 17/10* (2006.01)

(52) U.S. Cl.
CPC ............ *A61B 17/083* (2013.01); *A61B 17/085* (2013.01); *A61B 17/10* (2013.01); *A61B 17/105* (2013.01)

(58) Field of Classification Search
USPC ................. 606/213–217; 602/41–59
See application file for complete search history.

(56) References Cited

U.S. PATENT DOCUMENTS

| 345,541 A | 7/1886 | Reichardt |
| 363,538 A | 5/1887 | Penny |
| 1,774,489 A | 8/1930 | Sarason |
| 2,196,286 A | 4/1940 | Barsky |

(Continued)

FOREIGN PATENT DOCUMENTS

| DE | 2447681 | 4/1976 | ............... A61F 13/00 |
| EP | 0957774 | 6/2002 | ............... A61B 17/03 |

(Continued)

OTHER PUBLICATIONS

International Searching Authority, International Search Report—International Application No. PCT/2009/038188, dated Aug. 28, 2009, 5 pages.

(Continued)

*Primary Examiner* — Corrine M McDermott
*Assistant Examiner* — Alexander Orkin
(74) *Attorney, Agent, or Firm* — Remenick PLLC

(57) ABSTRACT

The present invention is directed to tissue closure devices for closing a tissue opening, including one or more closure components, each closure component having a first member and a second member, each of the first and second members having a first surface that adheres to a tissue surface proximate to the tissue opening, each of the first and second members having a second surface substantially orthogonal to the first surface, and each of the first and second members having a transitional region between the first surface and the second surface which is contoured to evert an edge of the tissue opening upon the drawing together of the first and second members. The present invention is also directed to systems and kits, dressing systems, and methods for tissue repair and closure.

9 Claims, 39 Drawing Sheets

Related U.S. Application Data

(60) Provisional application No. 60/522,207, filed on Aug. 31, 2004, provisional application No. 60/593,236, filed on Dec. 26, 2004, provisional application No. 60/594,771, filed on May 5, 2005.

(56) References Cited

U.S. PATENT DOCUMENTS

| | | | | |
|---|---|---|---|---|
| 3,288,137 | A | 11/1966 | Lund | |
| 3,863,640 | A | 2/1975 | Haverstock | 128/335 |
| 3,926,193 | A | 12/1975 | Hasson | 128/335 |
| 3,971,384 | A | 7/1976 | Hasson | 128/335 |
| 3,983,878 | A | 10/1976 | Kawchitch | 128/335 |
| 4,114,624 | A | 9/1978 | Haverstock | 128/335 |
| 4,141,363 | A | 2/1979 | James et al. | 128/335 |
| 4,423,731 | A | 1/1984 | Roomi | 128/335 |
| 4,467,805 | A | 8/1984 | Fukuda | 128/334 |
| 4,526,173 | A | 7/1985 | Sheehan | 128/335 |
| 4,535,772 | A | 8/1985 | Sheehan | 128/337 |
| 4,539,990 | A | 9/1985 | Stivala | 128/335 |
| 4,605,005 | A | 8/1986 | Sheehan | 128/335 |
| 4,702,251 | A | 10/1987 | Sheehan | 128/335 |
| 4,815,468 | A | 3/1989 | Annand | 128/335 |
| 4,924,866 | A | 5/1990 | Yoon | 128/335 |
| 4,973,466 | A | 11/1990 | Reich | 424/426 |
| 5,176,703 | A | 1/1993 | Peterson | 606/216 |
| 5,259,835 | A | 11/1993 | Clark et al. | 602/48 |
| 5,263,973 | A | 11/1993 | Cook | 606/216 |
| 5,486,196 | A | 1/1996 | Hirshowitz et al. | 606/218 |
| 5,562,705 | A | 10/1996 | Whiteford | 606/215 |
| 5,571,138 | A | 11/1996 | Blomqvist et al. | 606/218 |
| 5,733,305 | A | 3/1998 | Fleischmann | 606/213 |
| 5,843,123 | A | 12/1998 | Brazeau | 606/213 |
| 6,010,524 | A | 1/2000 | Fleischmann | 606/213 |
| 6,106,544 | A | 8/2000 | Brazeau | 606/213 |
| 6,176,868 | B1 | 1/2001 | Detour | 606/215 |
| 6,329,564 | B1 | 12/2001 | Lebner | 602/41 |
| 6,559,350 | B1 | 5/2003 | Tetreault et al. | 602/42 |
| 6,596,917 | B2 | 7/2003 | Oyaski | 602/43 |
| 7,361,185 | B2 | 4/2008 | O'Malley et al. | 606/215 |
| 7,429,265 | B2 | 9/2008 | O'Malley et al. | 606/215 |
| 2002/0019649 | A1 | 2/2002 | Sikora et al. | 606/232 |
| 2005/0033215 | A1 | 2/2005 | Lebner | 602/54 |
| 2008/0027484 | A1 | 1/2008 | Lee et al. | 606/215 |
| 2009/0036922 | A1 | 2/2009 | Riskin et al. | 606/215 |
| 2011/0022082 | A1 | 1/2011 | Burke et al. | 606/214 |

FOREIGN PATENT DOCUMENTS

| | | | | |
|---|---|---|---|---|
| GB | 1401877 | 8/1975 | | A61B 17/08 |
| WO | WO 96/10954 | 4/1996 | | A61B 17/08 |
| WO | 96/29013 | 9/1996 | | A61B 17/03 |
| WO | WO 99/42146 | 8/1999 | | A61L 25/00 |
| WO | WO 01/40348 | 6/2001 | | C08G 63/00 |
| WO | WO 2006/026634 | 3/2006 | | A61B 17/08 |
| WO | 2012/151366 | 11/2012 | | A61B 17/03 |

OTHER PUBLICATIONS

International Searching Authority, International Search Report—International Application No. PCT/US2012/036265, dated Nov. 20, 2012, together with the Written Opinion of the International Searching Authority, 12 pages.

STEP 1: DOCTOR INSPECTS AND CLEANS WOUND

STEP 2: DOCTOR OPENS WOUND CLOSURE KIT BOX

STEP 3: DOCTOR REMOVES FLEXURE LOOP FROM
INDIVIDUAL SEALED PACK

STEP 4: DOCTOR PEELS AWAY PART OR ALL OF PRESSURE
SENSITIVE ADHESIVE (PSA) BACKING

STEP 5 AND 6: DOCTOR ADHERES FLEXURE LOOP TO SKIN AROUND WOUND AND BENDS LOOPS TO APPROXIMATELY CLOSE WOUND

STEP 7: DOCTOR REMOVES HANDHELD SETTING FOOT FROM INDIVIDUAL SEALED PACK

STEP 8: DOCTOR REMOVES MULTIPLE CLASP PACK FROM INDIVIDUAL SEALED WRAPPED

STEP 9: DOCTOR LOADS FIRST SINGLE-PIECE CLASP INTO HAND TOOL

STEP 10: DOCTOR USES HAND TOOL TO CARRY CLASP JUST OVER APPROXIMATE CENTER OF LACERATION

STEP 11: DOCTOR ADHERES CLASP TO BOTH SIDES OF WOUND OPENING

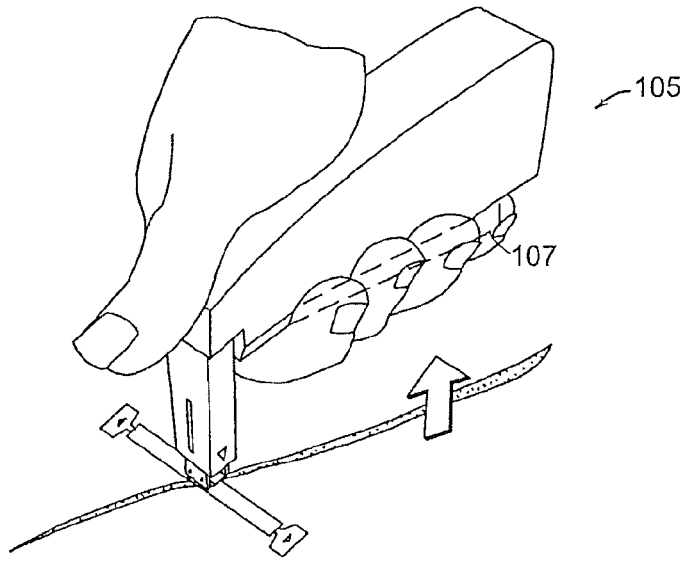

FIG. 17K STEP 12: AFTER CONFIRMING SATISFACTORY CLASP PLACEMENT ON BOTH SIDES OF WOUND, DOCTOR PULLS TRIGGER OF HAND-TOOL SETTING THE CLASP SPRING TO EVERT AND CLOSE THE WOUND

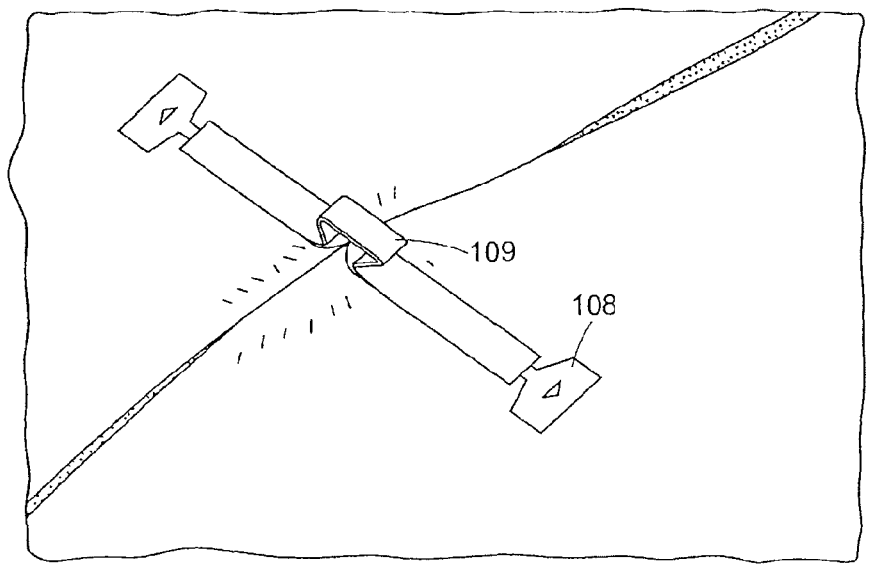

FIG. 17L STEP 13: DOCTOR INSPECTS CLOSURE AND EVERSION OF WOUND. IF NECESSARY, DOCTOR CAN PEEL UP AND REMOVE ENTIRE CLASP ASSEMBLY TO START AGAIN AT STEP 9. IF THE "STITCH" IS SATISFACTORY, THEN THE DOCTOR REPEATS STEPS 9 THROUGH 12 AS NEEDED.

STEPS 14 AND 15: AFTER INSPECTING ALL "STITCHES", CONFIRMING PROPER PLACEMENT, CLOSURE AND EVERSION, DOCTOR PULLS OUT BREAKAWAY CYANO-ACRYLATE (CA) PULL-TABS TO PERMANENTLY ADHERE CLASP ASSEMBLIES TO SKIN

- PERFORATIONS ALLOW FOR 1UP, 2UP & 3UP PLACEMENT
- ENTIRE DEVICE IS PSA BACKED AND BACKING PEELS AWAY

- SHADED CENTER PORTION OF BACKING IS PEELED AWAY FIRST
- DEVICE IS PRE-ADJUSTED FOR WIDTH SO THAT DEVICE EDGES LINE UP WITH WOUND EDGES

- REMAINING BACKING IS REMOVED
- DEVICE IS PLACED ACROSS WOUND IN ITS SLACKENED STATE

- DISPOSABLE PLASTIC TOOL IS USED TO GRIP DEVICES AND BRING THEM TOGETHER
- DEVICE RATCHETS TOGETHER APPLYING EQUAL TENSION TO BOTH SIDES OF WOUND
- WOUND EDGES ARE APPOSED AND WOUND IS CLOSED
- CENTRAL PORTION IS EVERTED
- CA IS RELEASED INTERNALLY

STEP 1: DOCTOR INSPECTS AND CLEANS WOUND

STEP 2: DOCTOR OPENS WOUND CLOSURE KIT BOX

STEP 3: DOCTOR REMOVES INDIVIDUAL CLASP PAIR FROM INDIVIDUALLY SEALED CLASP DISPENSING ROLL

STEP 4: DOCTOR REMOVES PSA BACKING STRIP

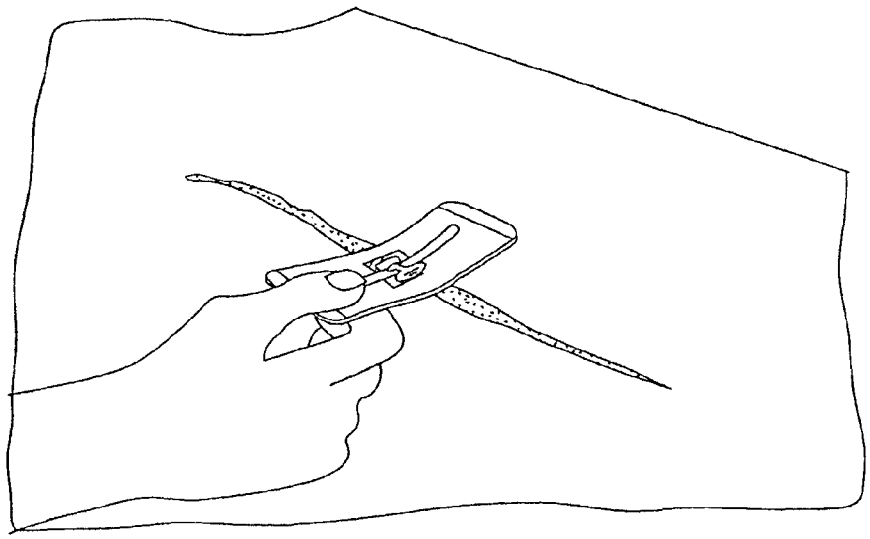

STEP 5: DOCTOR ADHERES PAIR TO ONE SIDE OF THE
WOUND APPROXIMATELY HALF WAY ALONG THE WOUND

FIG. 19E

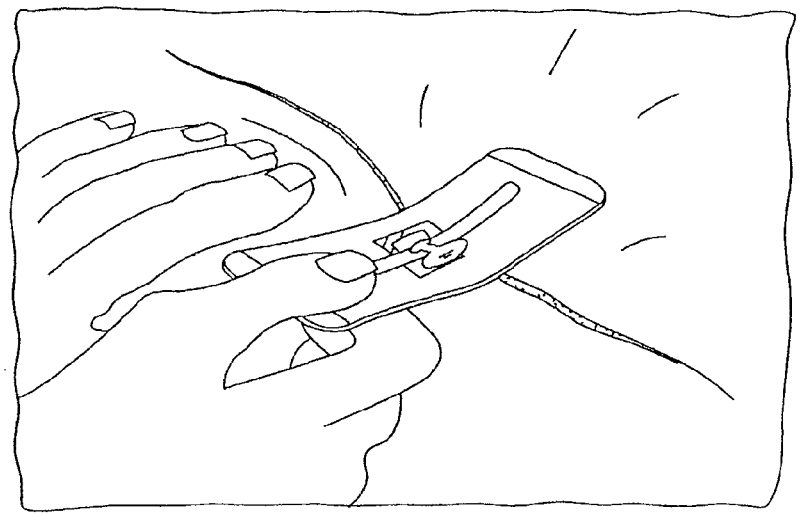

STEP 6: DOCTOR USES ONE HAND TO PUSH UN-ADHERED
SIDE OF WOUND WHILE PULLING THE ADHERED SIDE
WITH THE SECOND HAND UNTIL CLOSURE AND
ALIGNMENT IS ACHIEVED
STEP 7: (NOT SHOWN); DOCTOR ADHERES SECOND SIDE OF
CLASP-PAIR TO THE OTHER SIDE OF THE WOUND.
STEP 8: DOCTOR INSPECTS PLACEMENT AND ALIGNMENT
AND IF UNSATISFIED CAN PEAL BACK EITHER SIDE
FOR RE-POSITIONING AND RE-APPLYING

FIG. 19F

STEP 9: DOCTOR REPEATS STEPS 3 THROUGH 8 UNTIL
WOUND IS ALIGNED AND CLOSED SATISFACTORILY

STEP 10: DOCTOR PULLS OUT CENTRAL CLASP-PAIR TAB
ACTIVATING EVERSION AND FINAL CLOSURE FOR
EACH CLASP-PAIR

STEP 11: (NOT SHOWN); DOCTOR INSPECTS WOUND FOR FINAL ALIGNMENT, CLOSURE AND EVERSION
STEP 12: FOR EACH CLASP-PAIR DOCTOR PEELS UP AND REMOVES OUTER ADHERED AREA, ACTIVATING CA DISPENSING TO BOTH CLASP SIDES, PERMANENTLY ADHERING CLASP PAIR

STEP 1: DOCTOR ALIGNS HAND TOOL OVER WOUND SO THAT THE INNER TOOL EDGE IS ALIGNED WITH THE WOUND EDGE. THIS WILL SUPPORT ALIGNMENT OF CENTER OF CLOSURE STRIP OVER THE WOUND EDGE

STEP 2: DOCTOR SQUEEZES TRIGGER TO RELEASE EDGE OF CLOSURE STRIP AND LAYS EDGE ON SKIN PSA UNDER CLOSURE STRIP ADHERES TO SKIN

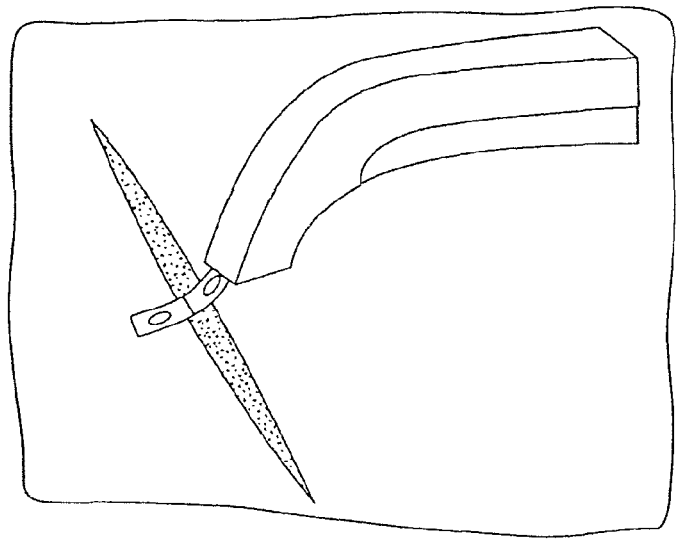

STEP 3: AS STRIP IS PULLED OUT OF THE PLACEMENT TOOL, IT PASSES BETWEEN ROLLER BALLS, SQUEEZING THE CLOSURE STRIP. THIS PRESSURE BREAKS THE THE INTERNAL CYANOACRYLATE BAGS AND FLATTENS THE INTERNAL PLASTIC WHICH WILL ULTIMATELY CREATE SKIN EDGE EVERSION. THE CLOSURE STRIP PULLS THE WOUND CLOSED AND FIRING THE TOOL RELEASES THE FINAL EDGE OF THE CLOSURE STRIP

FIG. 20C

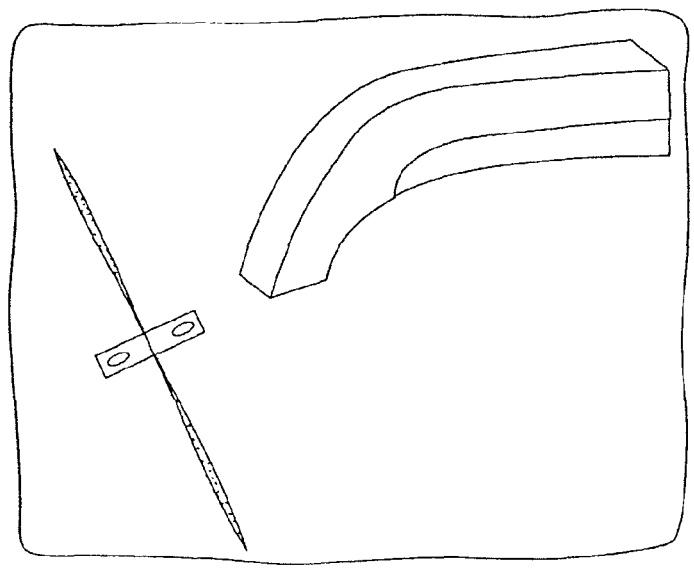

STEP 4: DOCTOR INSPECTS ALIGNMENT AND REMOVES STRIP IF UNSATISFACTORY

FIG. 20D

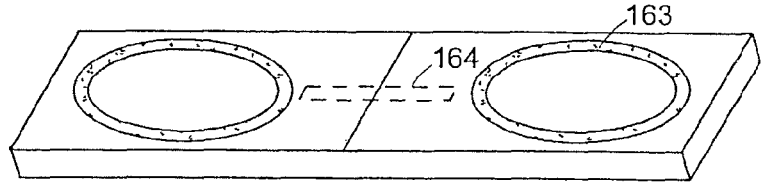

STEP 5: THE CLOSURE STRIP ITSELF IS COMPOSED OF TWO THIN PIECES OF FOAM TAPE OR NEOPRENE, ONE ON TOP OF ANOTHER, TO FORM A TOTAL THICKNESS OF 1.5 MM. BETWEEN THESE TWO ELEMENTS SIT TWO CYANOACRYLATE FILLED BAGS (ONE FOR EACH SIDE OF THE WOUND) AND ONE PLASTIC EVERSION PIECE (IN THE MIDDLE OF THE STRIP). THE BAGS ARE BROKEN AS THEY ARE RELEASED THROUGH THE PLACEMENT TOOL AND CYANOACRYLATE SLOWLY WICKS THROUGH THE UNDERSURFACE OF THE FOAM TAPE TO FORM A FINAL BOND WITH THE SKIN

FIG. 20E

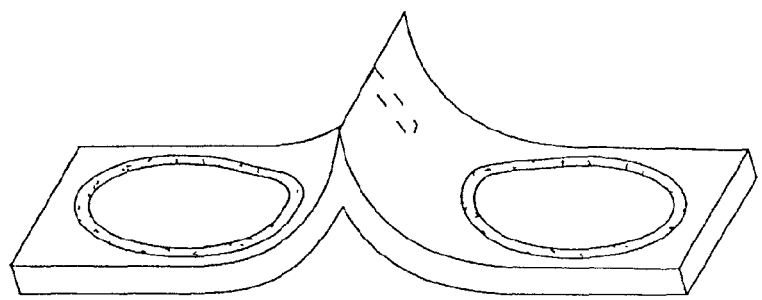

STEP 6: AFTER RELEASE FROM THE PLACEMENT TOOL, THE EVERSION PIECE WHICH SITS AT THE CENTER OF THE STRIP IS NO LONGER STRETCHED FLAT AS IT WAS WHILE PASSING THROUGH THE TOOL. IT RETURNS TO ITS RELAXED ARCHED POSITION, BRINGING THE WOUND EDGE INTO EVERSION

FIG. 20F

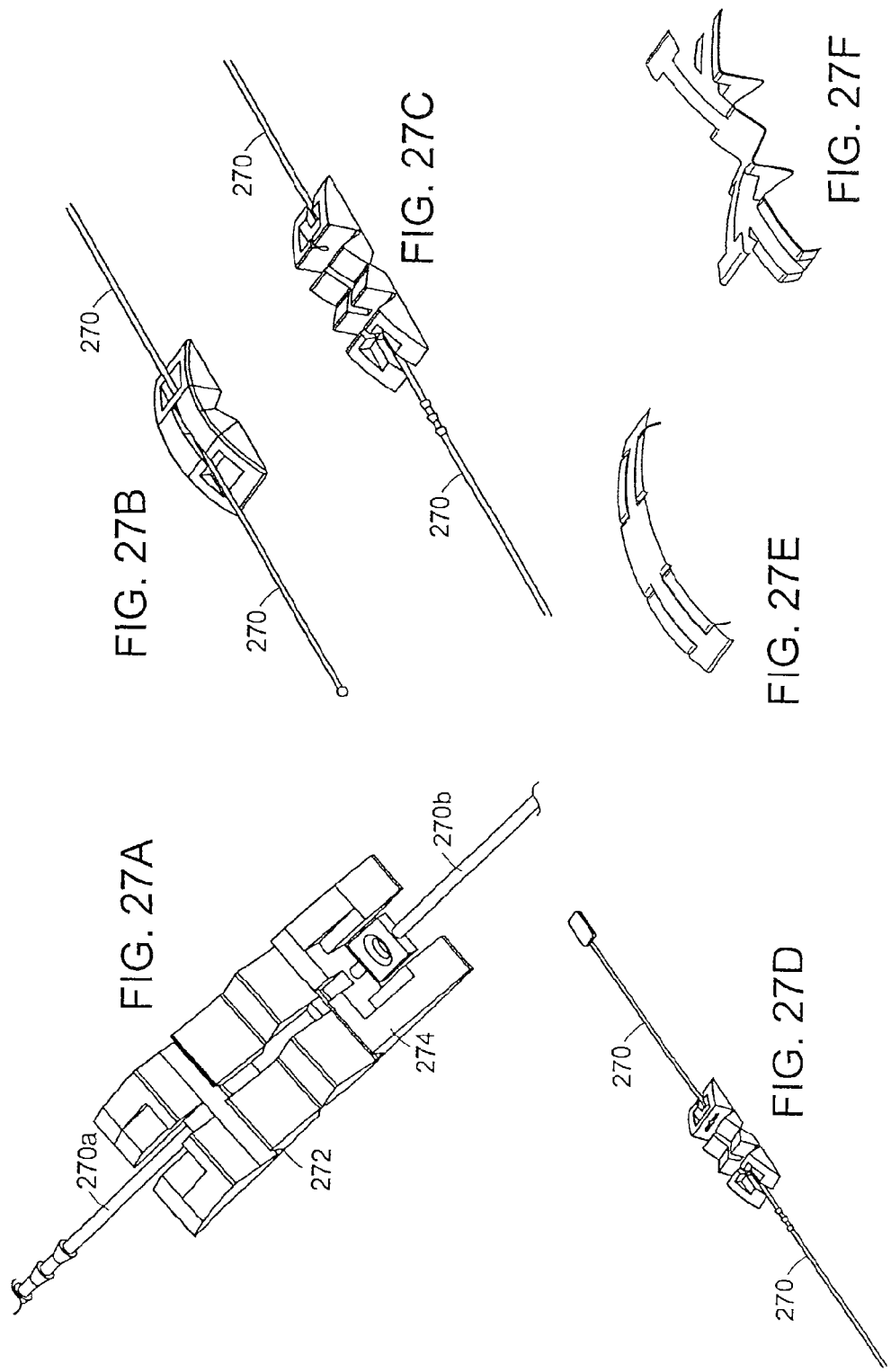

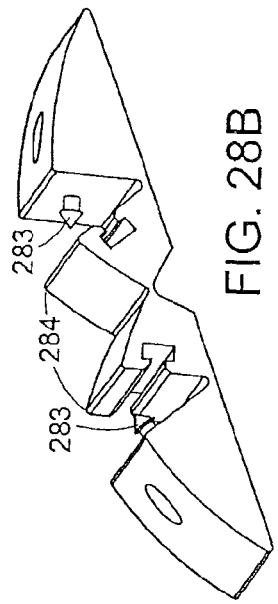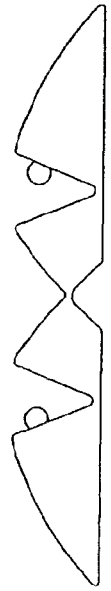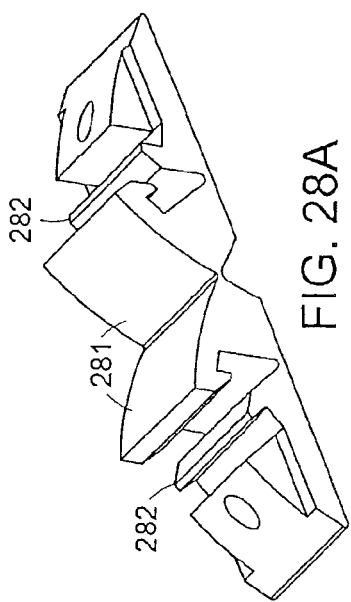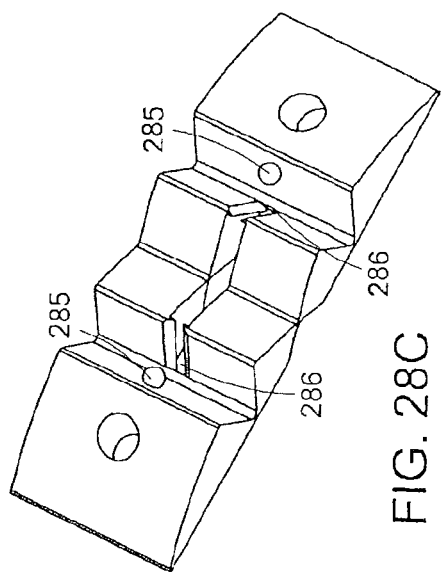

SYSTEMS AND METHODS FOR CLOSING A TISSUE OPENING

CROSS-REFERENCE TO RELATED APPLICATIONS

The present application is a continuation of U.S. patent application Ser. No. 12/059,485 filed Mar. 31, 2008, now U.S. Pat. No. 8,157,839, which in turn is a continuation in part of U.S. patent application Ser. No. 11/217,127 filed Aug. 31, 2005, which in turn claims the benefit of: U.S. Provisional Patent Application Ser. No. 60/522,207 filed Aug. 31, 2004; U.S. Provisional Patent Application Ser. No. 60/593,236 filed Dec. 26, 2004; and U.S. Provisional Patent Application Ser. No. 60/594,771 filed May 5, 2005. Each of the above-described applications are hereby incorporated herein by reference in its entirety.

TECHNICAL FIELD

This invention relates generally to tissue closure devices, systems and kits, dressing systems, and methods for tissue repair and closure.

BACKGROUND

Closure of tissue openings, such as, for example, for surgical incisions and accidental lacerations or wounds, is critical both to minimize the risk of infection and to promote optimal healing of the wound or incision. Both of these outcomes require rapid wound closure and careful skin edge approximation. Closing a tissue opening or wound requires a mechanism for drawing both sides of a tissue opening together to promote healing and to reduce the formation of scar tissue.

Previous wound closure systems included various categories of materials passed through the skin, such as staples and sutures, substances that cover skin edges and hold them adjacent, such as glues, and adherent structures, such as strips. Common methods for closing tissue openings caused by lacerations or surgical incisions are suturing and stapling. Both of these procedures are invasive, which can traumatize and compromise the integrity of the tissue opening and the nutrient blood supply to the healing tissue edges. They cause pain, increase the possibility of infection, expose the surgeon, as well as the patient, to blood-born disease, leave behind scars, and require a follow-up visit for suture or staple removal. Surgical glue is also used, but has only been proven adequate for small wounds where skin edges are not widely separated or under tension during closure.

Surgeons have become skilled in the various techniques of suturing to minimize the resulting blemish that occurs during the healing process. These methods require a threshold of dexterity that many care providers do not possess. This is particularly true in emergency situations, which often require immediate treatment to secure the tissue opening to allow for transport or until such time as proper surgery is possible. Suturing, even by a skilled surgeon, punctures and stresses tissue causing scarring. A sutureless tissue opening closure system would be a great benefit in many situations.

Adhesive tissue closures have been introduced that can effectively close some types of tissue openings without inflicting the additional injury inherent in suturing. Adhesive closures have a backing to provide solid structure, and have an adhesive layer for adhering to the skin.

An exemplary early attempt in non-invasive wound closures used a pair of strips of fabric having adhesive backing. The strips of fabric were applied in parallel on either side of the tissue opening and were constructed with threads extending transversely to bridge the tissue opening. A compressive force was applied across the tissue opening by tying opposing ends of the transverse threads of adjacent strips.

In another device, the distal ends of the bridging threads of one adhesive strip were interconnected by another pulling strip, allowing the bridging threads to be manipulated in concert. This configuration required that the bridging threads or filaments of each of the adhesive strips be interlaced to enable the pulling strips to be pulled across the tissue opening and secured.

However, as with many prior systems, the manipulation of a loose assembly of multiple parts in an emergency and possibly life-threatening situation is a challenging undertaking.

In addition, some adhesives have been used that have utility for skin contacting applications, provide good skin compatibility, and are hydrophobic, so that they tend not to remain in the interior of tissue openings. However, their tensile strength is only sufficient for some uses, for example, for closing or sealing skin cracks, not for holding major tissue openings closed against the range of motion to which the skin or any tissue is normally subjected.

In addition to the typical wound closure devices, referred to also as devices to close a tissue opening herein, other aspects of wound closure and care have deficiencies. For example, kits for wound irrigation and closure do not allow the introduction of sterile or clean fluids before beginning a procedure. They also do not allow for different sections to be cleaned or sterilized for different parts of the procedure. Post procedural care is critical to achieve optimal healing results, but is often not properly attended to in order to minimize scarring and optimize wound healing. Currently available wound dressings are not specialized for different time periods within the healing cycle. By ignoring the changing physiology and needs of the healing wound, current dressings do not provide an optimal healing environment.

There is still a need to simplify and improve upon devices and methods for closing tissue openings and their application and provide for wound care in general.

SUMMARY OF THE INVENTION

The systems and methods for closing surgical incisions and non-surgical wounds of various embodiments of the invention provide for improved wound care.

One aspect of the invention provides for a closure device for closing a tissue opening, including one or more closure components, each closure component having a first member and a second member, each of the first and second members having a first surface that adheres to a tissue surface proximate to the tissue opening, the first surface having at least one adhesive, each of the first and second members having a second surface substantially orthogonal to the first surface and having at least one connective element on the second surface, and each of the first and second members having a transitional region between the first surface and the second surface which is contoured to evert an edge of the tissue opening upon the drawing together of the first and second members by the engagement of at least one connective element.

In some embodiments, the connective element is a locking mechanism. In various embodiments, the locking mechanism includes a locking member extending from the second surface of the first member and the second surface of the second member having a receiving member. In one embodiment, each of the second surfaces has at least one locking member and at least one receiving member, such that in some embodiments, the first member and the second member are identical. In one embodiment, the connective elements include a ball and socket mechanism. In another embodiment, the connective elements include a ball and slot mechanism. In another embodiment, the connective elements include a ratchet mechanism. In yet another embodiment, the connective elements include a suture ligature, and in another embodiment, the connective elements have a lock and key mechanism. In some embodiments, the connective elements include magnets. In additional embodiments, the connective elements have a photobonded mechanism. In one embodiment, the connective elements include a staple. In some embodiments, the connective element of the first member engages the connective element of the second member when the second surface of the first member is in operative relation to the second surface of the second member. In various embodiments, the engaged connective elements provide a vertical force orthogonal to a plane of the tissue opening on at least one edge of the tissue opening. In further embodiments, the process of engaging the connective elements brings edges of the tissue opening together and everts the edges of the tissue opening. In one embodiment, the connective element is an adhesive, which in some embodiments is glue.

In some embodiments, the first and second members are releasably coupled. In some embodiments, the closure device further includes a closure release mechanism. In one embodiment, the closure release mechanism is a push button release hole.

In some embodiments, the closure device further includes a mechanism to adjust the placement of the members. In various embodiments, the mechanism to adjust the placement of the members is a sliding track. In additional embodiments, the mechanism to adjust the placement of the members is the adhesive on the first surface providing for repositioning of the member. In further embodiments, the mechanism to adjust the placement of the members is a hinge. In some embodiments, the mechanism to adjust the placement of the members is a ball bearing. Furthermore, in some embodiments, the mechanism to adjust the placement of the members includes an element to secure its position and prevent or at least minimize further unintended adjustment. In various embodiments, the securing element is mechanical, and in some embodiments the securing element is an adhesive.

In various embodiments, the closure device further includes a sliding lock to position and hold the first and second members in proximity to each other. In some embodiments, the closure device further has protrusions extending from the member to facilitate handling of the components. In additional embodiments, the closure device further includes an elastomeric base between the adhesive and the first surface of at least one member.

In some embodiments, the members, or a portion of the members, are plastic. In other embodiments, the members, or a portion of the members, are metal. In some embodiments the members are bioabsorbable. Furthermore, in some embodiments, at least one of the members is flexible.

In additional embodiments, the closure device further includes an agent to detect at least one of the presence of an infection or the presence of an impending infection. In some embodiments, the agent is present in a covering placed over the tissue opening. In various embodiments, the agent is present in at least one member.

In some embodiments, the adhesive is a semi-permanent skin bonding agent. In various embodiments, the semi-permanent skin bonding agent is a pressure sensitive adhesive. In other embodiments, the semi-permanent skin bonding agent is a skin glue. Further, in some embodiments, the closure device further comprises a second adhesive, such as for example, cyanoacrylate, or other biological glue, or a pressure sensitive adhesive. A non-limiting example of a biological glue is a thrombin gel. In some embodiments, at least one member comprises an opening for application of a second adhesive provided in a plane that is substantially parallel to the first surface and spaced apart from the first surface, the opening extending through to the first surface, and in some embodiments the opening is for application of a second adhesive. In some embodiments, the opening does not extend through the first adhesive.

In some embodiments, each member comprises two or more layers. In further embodiments, at least one layer is porous. In additional such embodiments, the porous layer is sealed by a material that provides pressure-induced porosity. In some embodiments, the second adhesive is present in the porous layer.

In various embodiments of the invention, the transitional region is tapered. In some embodiments, the transitional region is beveled. In other embodiments, the transitional region is arcuate. In further embodiments, the transitional region is chamfered, and in yet further embodiments, the transitional region is sloped.

Another aspect of the invention provides for a kit for a wound closure system, including a container having, a first component or layer of materials for cleaning a tissue opening; and a second component including a closure device, wherein at least two of the components of the kit are physically separated.

In some embodiments, the materials for cleaning the tissue opening include an irrigation system. In various embodiments, the irrigation system includes a container of saline and a non-splash syringe.

In some embodiments, the closure device includes one or more closure components, each closure component having a first member and a second member; each of the first and second members having a first surface that adheres to a tissue surface proximate to the tissue opening, the first surface having at least one adhesive; each of the first and second members having a second surface substantially orthogonal to the first surface and having at least one connective element on the second surface; and each of the first and second members having a transitional region between the first surface and the second surface which is contoured to evert an edge of the tissue opening upon the drawing together of the first and second members by engaging the connective elements. In some embodiments, each member of the closure device has two or more layers. In additional embodiments, at least one layer is porous. In some embodiments, the porous layer is sealed by a material that provides pressure-induced porosity. In further embodiments, the second adhesive is present in the porous layer. In additional embodiments, the closure device includes suturing materials.

In various embodiments, the kit further includes a component having instructional materials. In further embodiments, the kit further includes a sterile field component. In some such embodiments, the sterile field component includes sterile gloves, and in further such embodiments, the sterile field component includes a sterile field to allow preparation for a sterile tissue closure procedure. In some embodiments, the components subsequent to the sterile field component are sterile.

In additional embodiments, the kit further includes materials for application of an adhesive. In some embodiments, the materials for application of an adhesive include at least one of an applicator tip, an adhesive, and an adhesive dispenser. In some embodiments, the adhesive is cyanoacrylate.

In some embodiments, the container is a sealed tray. In additional embodiments, at least a portion of the container is covered by a removable barrier. In various embodiments, removing the removable barrier provides a window to a specific component of the kit. In further embodiments, the kit further has an external cover. In some such embodiments, the container defines an opening for access to at least a portion of the container, which opening is covered by the external cover. In various embodiments, a fluid can be introduced into at least a portion of the container through the opening. Furthermore, in some embodiments, the container comprises a receptacle for receiving the fluid.

According to another aspect, the invention provides for a dressing system to facilitate healing of a tissue opening, including one or more bandages for dressing a tissue opening, the bandages being appropriate for specific time periods of healing of a tissue opening, and at least one of the bandages having an additive to facilitate healing of a tissue opening.

In some embodiments, the dressing system further includes instructional material or a manual. In various embodiments the instructional material includes information regarding placement of one or more bandages at one or more specified time periods. In some embodiments, the time periods correspond to phases of healing.

In additional embodiments, at least one bandage prevents or at least minimizes the penetration of moisture to the tissue opening. In further embodiments, at least one bandage has an agent for pain relief. In some embodiments, at least one bandage includes an agent to detect at least one of the presence of an infection and the presence of an impending infection. In one embodiment, at least one bandage has an indicator responsive to changes associated with infection. In one such embodiment, the indicator reacts to at least one of a specific pH level or protein exudates.

In further embodiments, at least one bandage is transparent. In additional embodiments, at least one bandage has at least one agent to facilitate healing. In some embodiments, the agent to facilitate healing is Vitamin E. In yet further embodiments, at least one bandage includes agents to maximize scar softness and reduce discoloration. In some embodiments, at least one bandage has a solvent for removal of a closure device. In one embodiment, the dressing system has at least one bandage that prevents penetration of moisture to the tissue opening and at least one bandage comprising Vitamin E.

In some embodiments, the dressing system further includes a receptacle having at least one agent for application to the tissue opening or to at least one bandage.

Another aspect of the invention provides for a dual-adhesive closure device for closing a tissue opening, having one or more closure components, each closure component having a first member and a second member, each of the first and second members having a first surface that adheres to a tissue surface proximate to the tissue opening, the first surface having at least one adhesive, each of the first and second members having a second surface substantially orthogonal to the first surface and having at least one connective element on the second surface, each of the first and second members having a transitional region between the first surface and the second surface which is contoured to evert an edge of the tissue opening upon the drawing together of the first and second members by the engagement of the connective elements, and a second adhesive applied to secure the first surface to tissue approximately adjacent to at least one edge of the tissue opening.

In some embodiments, both members include a first layer, a second layer, and a reservoir between the first layer and the second layer, the reservoir containing the second adhesive. In various embodiments, the second adhesive is released when the connective elements are engaged. In additional embodiments, the second adhesive is applied manually. In further embodiments, the adhesive is released from a reservoir within the member. In some embodiments, the adhesive is applied from an external source and spreads between the first surface and an adjacent tissue surface. In various embodiments, the second adhesive is cyanoacrylate.

In some embodiments, each member of the dual-adhesive closure device comprises two or more layers. In additional embodiments, at least one layer is porous. In further embodiments, the porous layer is sealed by a material that provides pressure-induced porosity. In some embodiments, the second adhesive is present in the porous layer.

An additional aspect of the invention provides for a closure system for a tissue opening, including a temporary closure device comprising a deformable perimeter defining an opening, the deformable perimeter having a first surface and at least one adhesive on the first surface.

In some embodiments, the temporary closure device surrounds the tissue opening. In additional embodiments, the temporary closure device is oval. In various embodiments, the adhesive is present on two spaced sections of the first surface. In some embodiments, the adhesive is a pressure sensitive adhesive.

In various embodiments, the temporary closure device, or part thereof, is plastic. In additional embodiments, the temporary closure device includes sections of material forming the perimeter, the perimeter having at least one material in each section, the perimeter further having nonidentical sets of materials used in at least two sections, and wherein the sections with nonidentical sets of materials are not adjacent.

In further embodiments, the temporary closure device is sufficiently compliant to deform and exert pressure on opposing sides of a tissue opening and is sufficiently rigid to maintain the deformed shape and maintain the pressure on opposing sides of the tissue opening. In some embodiments, opposing sides of the perimeter are pressed together, exerting a force on tissue underneath the temporary closure device to bring edges of a tissue opening closer together.

In some embodiments, the closure system further includes a closure device, having one or more closure components, each closure component including a first member and a second member, each of the first and second members having a first surface that adheres to a tissue surface proximate to the tissue opening, the first surface having at least one adhesive, each of the first and second members having a second surface substantially orthogonal to the first surface and having at least one connective element on the second surface, and each of the first and second members having a transitional region between the first surface and the second surface which is contoured to evert an edge of the tissue opening upon the drawing together of the first and second members by the engagement of the connective elements.

In some embodiments, each member of the closure device has two or more layers. In additional embodiments, at least one layer is porous. In further embodiments, the porous layer is sealed by a material that provides pressure-induced porosity. In some embodiments, a second adhesive is present in the porous layer.

In various embodiments, the closure system further includes an applicator device for applying the closure components, the applicator device comprising at least one of a mechanism to hold the closure components, a mechanism to release the closure components, and a mechanism to affix the closure components. In some embodiments, the applicator device has a handle, a plunger, and/or a reservoir. In additional embodiments, the reservoir holds an adhesive. In some embodiments, the mechanism to affix the closure components releases an adhesive. In additional embodiments, the applicator device further comprises a light-based guide to assist with the placement of the members. In additional embodiments, the applicator device further includes a mechanism to adjust placement of the closure components. In still additional embodiments, the applicator device further includes a mechanism for lowering the closure components onto the tissue surface. In some embodiments, the applicator device further includes a mechanism for securing the closure components. In additional such embodiments, the mechanism for securing the closure components comprises an adhesive released from the applicator device. In various embodiments, the adhesive is cyanoacrylate.

Another aspect of the invention provides for a method for closing a tissue opening, including positioning a closure device for closing a tissue opening, the closure device having one or more closure components, each closure component having a first member and a second member; each of the first and second members having a first surface that adheres to a tissue surface proximate to the tissue opening, the first surface having at least one adhesive, each of the first and second members having a second surface substantially orthogonal to the first surface and having at least one connective element on the second surface, and each of the first and second members having a transitional region between the first surface and the second surface which is contoured to evert an edge of the tissue opening upon the drawing together of the first and second members by the engagement of the connective elements; drawing the first and second members into proximity such that the connective element on the second surface of the first member engages the connective element on the second surface of the second member; and securing each of the first and second members to a tissue surface.

In some embodiments of the invention, the closure members are positioned adjacent to an edge of the tissue opening. In additional embodiments, the transitional region is tapered. In further embodiments, edges of the tissue opening adhere to the transitional region and are everted. In some embodiments, bringing the first and second members into proximity such that the connective element on the second surface of the first member engages the connective element on the second surface of the second member everts the wound edge. In one embodiment, the transitional region is beveled and drawing the first and second members into proximity such that the connective element on the second surface of the first member engages the connective element on the second surface of the second member brings the beveled transition region of the first member into proximity with the beveled transition region of the second member and everts the wound edge.

Additional embodiments of the method further include adjusting the position of at least one of the closure members after positioning it. In some embodiments, the first and second members are secured before bringing them into proximity. In other embodiments, the first and second members are secured after bringing them into proximity. In various embodiments, the first and second members are secured with an adhesive. In some embodiments, the adhesive is cyanoacrylate. In further embodiments, the adhesive is released from at least one member. In yet additional embodiments, the adhesive is released from the members when the connective elements of the first and second members engage. In some embodiments, each member comprises two or more layers, at least one layer being porous. The porous layer is sealed by a material that provides pressure-induced porosity. In further embodiments, each member includes two or more layers, at least one layer being porous, wherein the adhesive is present in the porous layer.

In further embodiments, the two or more closure components are positioned in spaced relationship ranging from approximately 1 mm to approximately 5 cm, and in a preferred embodiment ranging from approximately 1 mm to approximately 1 cm.

In some embodiments, the method further includes affixing the positioned members. In some embodiments, the members are affixed with an adhesive. In one embodiment, the adhesive is a pressure sensitive adhesive, and in another embodiment, the adhesive is glue.

Additional embodiments further include bringing the edges of the tissue opening into proximity prior to positioning the closure members. In some embodiments, the edges of the tissue opening are brought into proximity using a temporary closure device comprising a deformable perimeter defining an opening, the deformable perimeter having a first surface and at least one adhesive on the first surface. In additional such embodiments, the temporary closure device surrounds the tissue opening. In further such embodiments, the method further includes pressing opposing portions of the perimeter towards each other thereby exerting a force on tissue underneath the temporary closure device to bring edges of a tissue opening closer together. In an alternate embodiment, one or more closure members is placed in proximity to the tissue opening prior to the use of a temporary closure device. Some embodiments are designed such that the wound closure members are applied and fastened by one person. This is in contrast to conventional wound closure devices that include, for example, staples, glues, and strips, which are generally preferably applied and fastened or closed by two people.

Another aspect of the invention provides for a closure device for closing a tissue opening, including one or more closure components, each closure component having a member; the member having a first surface that adheres to a tissue surface proximate to the tissue opening, the first surface having at least one adhesive; and the member including an eversion element, the eversion element contoured to evert an edge of the tissue opening upon the application of the closure component. In an embodiment, the eversion element is a resilient member, for example, a spring mechanism.

In some embodiments, the adhesive is a semi-permanent skin-bonding agent. In further embodiments, the semi-permanent skin-bonding agent is a pressure sensitive adhesive. In additional embodiments, the semi-permanent skin-bonding agent is a skin glue.

In various embodiments, the member has a first layer and a second layer. In some embodiments, the closure device has a reservoir between the first layer and the second layer, the reservoir containing a second adhesive. In some embodiments, the second adhesive is cyanoacrylate. In additional embodiments, at least one layer is porous. In further embodiments, at least a portion of the porous layer is sealed by a material that provides pressure-induced porosity. In further embodiments, a second adhesive is present in the porous layer In some embodiments, the invention provides for the use of the devices, methods, kits, and systems described herein for the treatment and/or closure of a tissue opening or in the manufacture of a device, kit or system for the treatment or closure of a tissue opening.

In one aspect, the invention is a closure device for closing a tissue opening, including one or more closure components, each closure component comprising a first member and a second member, each of the first and second members having a first surface that adheres to a tissue surface proximate to the tissue opening. The first surface has at least one adhesive. Each of the first and second members have a second surface that has at least one alignment member positioned therein and in a portion of the body of the respective member, the second surface and body of each member being further structured to receive a second alignment member. Each of the first and second members have a transitional region between the first surface and the second surface which is contoured to evert an edge of the tissue opening upon the drawing together of the first and second members by the engagement of the at least one alignment member.

In other aspects, each of the alignment members has a locking mechanism. In some aspects, the first member and the second member are identical. In some aspects, the alignment members include at least one of a ball and socket mechanism, a ball and slot mechanism, a ratchet mechanism, a suture ligature, magnets, a photobonded mechanism, a staple, and a lock and key mechanism. In some aspects, the alignment members are ratchet mechanisms including a plurality of teeth. In some aspects, the first and second members are releasably coupled. In some aspects the plurality of teeth are non-uniform in height. In some aspects, each alignment member of each closure component has three teeth, wherein the tooth on each of the alignment member farthest from the second surface of each of the alignment member has a height greater than the other two teeth on each of the alignment member. In other aspects, the members further comprise a second adhesive. In further aspects, the alignment members are positioned substantially in a lower one third portion of the at least first and second members with respect to the height dimension of the at least first and second members. In some aspects, the vertical height of the teeth is in the range of approximately 0.005 cm to approximately 0.1 cm. In other aspects, the teeth of each alignment member are positioned closer to the second surface of that member than to the end of the alignment member as measured along a principle axis of the alignment member. In yet other aspects, the locking mechanism comprises a hollow section for engagement of the teeth.

In another aspect, the invention is a method for closing a tissue opening, including positioning a closure device for closing a tissue opening, the closure device comprising one or more closure components, each closure component comprising a first member and a second member. Each of the first and second members have a first surface that adheres to a tissue surface proximate to the tissue opening, the first surface having at least one adhesive. Each of the first and second members include a second surface having at least one alignment member positioned therein and in a portion of the respective first and second members. The second surface and portion of the first and second members being further structured to receive a second alignment member. The method includes drawing the first and second members into proximity such that each first member receives the alignment member of each second member and each second member receives the alignment member of each first member. Further, the method includes everting an edge of the tissue opening upon the drawing together of the first and second members, the first and second members having a transitional region between the first and second surfaces which is contoured to evert an edge of the tissue opening. The method includes the step of securing each of the first and second members to a tissue surface.

In some aspects, each of the alignment members further comprises a locking mechanism. In other aspects, the alignment members are ratchet mechanisms including a plurality of teeth. In some of these aspects, the locking mechanism comprises a hollow section for engagement of the teeth. In other aspects, the alignment members provide a vertical force substantially orthogonal to a plane of the tissue opening on at least one edge of the tissue opening. In yet other aspects, the alignment members are positioned substantially in a lower one third portion of the at least first and second members with respect to the height dimension of the first and second members. Further, in some aspects, the vertical height of the teeth is in the range of approximately 0.005 cm to approximately 0.1 cm.

Reliable skin eversion in certain embodiments is obtained by closure members that contain self-aligning balanced pull tabs that are integral to closing a wound. In some embodiments, a tissue opening is treated and/or closed with one or more pairs of members, each member of a pair being engaged with the other member of the pair to facilitate wound treatment. As an example, in some aspects, two identical members are used to treat a tissue opening, each member containing both a pull tab and an opening for receiving and locking the pull tab from the other member. In other embodiments, the members are not identical. When the members are applied to the tissue and the pull tab from each member is inserted through the opening of the paired member, the structure of the pull tabs allows the two members to remain in alignment.

The action of pulling the pull tabs draws the paired members towards each other and causes the edges of the tissue opening to be brought toward each other. The pull tabs and member openings that receive pull tabs further allow certain embodiments to be effectively applied to tissue openings of varying sizes. It is preferred that the tissue opening to be treated is smaller than the length of the pull tabs. However, even for a tissue opening larger than the length of the pull tabs, the members can be applied to both sides of the opening and manually brought together to allow the pull tabs to engage with the respective openings on paired members. A further benefit of certain embodiments of the invention is that wounds can be closed over the course of multiple application steps. The person applying the tissue closure devices of the invention can choose to engage the members and close the wound either partially or fully.

Some embodiments are further fitted with locking mechanisms that releasably lock a pull tab of a first member in an opening of a paired member. Such locking mechanisms can be unlocked by a tool, for example a tweezer or a needle, and the locks can subsequently be reengaged on the pull tab to relock the pull tab. The releasable locks allow for drainage of wound edema and/or the treatment of infection, without removal and reapplication of the device. Such a feature can also be helpful when a wound needs to be temporarily left open to facilitate healing.

In some aspects, the locking mechanism includes a hollow recess. A tool, for example a needle, can be used to unlock the locking mechanism, for example by engaging the end of the needle into the hollow recess of the locking mechanism, applying force to the locking mechanism through the tool, and with that force unlocking the locking mechanism.

Some embodiments are further provided with at least one programmed adhesive. Programmed adhesives are designed to lose the functionality of the adhesive after a programmed period of time or range of time. Using such adhesives, a wound can be healed and treated with closure members designed to lose their adhesive characteristic with the skin after some period of time, in some cases obviating the need for a trained medical professional to remove the closure members.

There are numerous advantages to the various embodiments of the invention. One advantage of some embodiments of the invention is that the wound closure components of the invention can be quickly and easily affixed to wound skin edges and aligned for proper orientation. The components are placed at intervals along a wound before closure. Paired opposing components attach to each other to bring skin edges into proximity. When opposing members are attached to each other, they form a bridge to approximate that section of the wound and provide an optimal environment for wound healing. The members provide vertical force orthogonal to the wound plane, thereby creating wound edge eversion to promote healing. In some cases, the components contain a locking mechanism to allow opposing components to form a tight bond. Another advantage to the various embodiments of the invention is the routine and reliable skin eversion that does not require expertise in the medical art.

Some embodiments achieve improved wound edge eversion by leveraging the geometric relationships of paired components. In some embodiments, each closure member has a portion designed to make contact with a portion of a paired member, the contacting area of each member further serving as a pivot. As the pull tab of a first member is drawn through the connective opening of a paired member, and the pull tab of the paired member is substantially simultaneously drawn through the connective opening of the first member, the member bodies are drawn closer to each other. As the tabs continue to be pulled, the two members eventually make contact with each other at least at an edge that first makes contact. As the tabs continue to be pulled after the two members have made contact at the contact edge, the contact edge tends to move up in a direction away from the surface of the skin. This causes each of the members to rotate upwardly, away from the surface of the skin or wound. The bottom surface of the members are adhesively attached to a surface of the skin such that when the members rotate upwardly, the bottom surface of the members that are attached to the skin are lifted up by a vertical force substantially orthogonal to the plane of the wound. These upward forces on the wound edge create wound edge eversion that promotes healing of the wound. Wound edge eversion is facilitated by pull tabs that are preferably in the bottom one third portion of the closure members and contacting areas that are preferably in the top one third of the height of the closure members. The force acting on the wound closure members via the pull tabs is thus applied closer to the skin than the contact edge. This creates a pivot point or surface and a force applied generally orthogonal to the wound plane that facilitates wound edge eversion.

Similar to the functionality of the pivot described above, some embodiments are designed with multiple pivot points or surfaces. These provide the same function—to translate forces that are applied to the device in a direction along the surface of the skin (i.e. pulling the pull tabs) to forces provided to the edge of the skin in a direction substantially orthogonal to the wound surface (i.e. movement in an upward direction). This facilitates wound edge eversion and promotes healing of the wound and a reduction in the formation of scar tissue.

Another advantage of various embodiments of the invention is that the devices and methods provide gross alignment of skin edges, fine alignment of skin edges, targeted placement of adhesive closure components, and long term bonding of the adhesive closure components.

The methods of some of the embodiments of the present invention are also advantageous because they are directed to creating a comfortable working environment and improved step-appropriate sterility during a wound closure procedure. For example, a multilayer kit may offer an instruction layer, a cleaning layer, a sterile field layer, and/or a closure layer. Each layer may be distinct to allow appropriate levels of cleanliness or sterility, availability to pour and use necessary fluids, and a clean workspace for that step of the procedure. The closure layer contains a wound closure device or system. Another advantage is that a system is also provided for post-procedural care of the healing wound.

The foregoing and other features and advantages of the invention will be apparent from the following more particular description of the embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIGS. 17A-17M are representations of a method of using a kit for a closure system including the kit, various components contained within the kit, and a method of its use.

FIGS. 19A-19I are representations of a method of using a kit for a closure system including the kit, various components contained within the kit, and a method of its use.

FIGS. 20A-20F are representations of a closure device containing multiple wound closure components and a method of its use.

FIGS. 27A-27F are schematic views of closure component members that provide mechanical closure and skin edge eversion. In particular, FIGS. 27A, 27C and 27D illustrate views of the closure components before they are applied to a wound and closed. FIGS. 27B and 27F illustrate views of the closure components once they have been applied to a wound.

FIGS. 28A-28D are views of closure components according to another embodiment which allows for mechanical locking as well as skin eversion.

FIG. 30B is a view of the closure components in a mechanically locked position.

DETAILED DESCRIPTION

Figure 1:
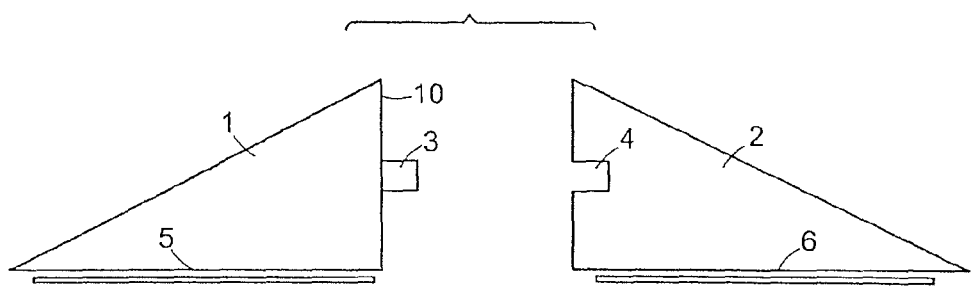
FIG. 1 is a schematic cross-section of a closure component.

Various embodiments of the invention relate to systems and methods for closing a tissue opening non-invasively. Additional embodiments of the invention relate to devices or kits structured to improve the process of wound closure. Further embodiments of the invention also relate to systems and devices for post-procedural wound care.

As used herein, a "wound" refers to any tissue opening, whether accidental or intentional, including but not limited to, a surgical incision, accidental laceration, or other form of injury. In various embodiments the wound is a tissue opening in the skin or other tissue. The wound may be in any animal, including human and non-human animals. In some embodiments, the wound is in a mammal or a non-human mammal.

By way of a non-limiting example, in some embodiments, a closure kit contains a treatment tray. The tray can have a multi-stage modular system for controlling the treatment environment. Unfolding packages within the tray creates a procedural field while maintaining critical aspects of the closure system close at hand for rapid use. This prevents the common scenario of a cluttered table with difficult to reach instruments.

In some embodiments, the needle-less or non-invasive closure system includes a set of clip-like devices designed to rapidly and easily close a wound by mechanical means. It can be applied to even large wounds in minutes, whereas sutures, the traditional alternative, often take up to an hour for placement. Some embodiments achieve wound closure through a "skin buckle" mechanism with rapid and simple placement through combination adhesives. Each closure member is positioned on either side of opposing laceration edges and initially secured in place by a pressure sensitive adhesive similar to tape. When the device is engaged, or buckled, the wound edges are mechanically drawn together and the wound is sealed. When fastened, the device releases a semi-permanent skin-bonding agent, creating a closure that will resist migration and dislodgement. When the wound is healed, the device falls off due to normal exfoliative processes; alternatively, the device can be removed easily and painlessly at the physician's discretion using acetone or another solvent commonly available.

Functional benefits of such a wound closure system that relies on a combination skin adhesive and mechanical device to bring skin edges together include, without limitation, ease of placement and elimination of needles. For large wounds, administration of local anesthesia, such as Novocain, commonly includes several needle punctures. Each administration, assuring wound numbness, is accompanied by a burning sensation at the injection site. Because no needles are necessarily used to place this device, no local anesthesia is necessary. The elimination of needles reduces pain and emotional distress for patients and associated disease transmission risk for healthcare providers. Furthermore, because various embodiments of the closure utilize a mechanical device rather than current tape-based (steri-strips) or uni-dimensional (stitches) processes, more control of outcome is obtainable. Scientific principles show that cosmetic outcome in wound healing is largely determined by apposition and eversion created during wound closure.

Apposition is the proper alignment of skin edges to prevent gaps or mismatch. By allowing the physician to place and replace the device using a pressure sensitive adhesive before a skin bonding agent is released, better or optimal apposition can be achieved with various embodiments of the invention than many common conventional methods and devices.

Eversion is the raising of skin edges during the initial healing process. This is critically important as expected scar formation includes myofibril contraction, which ultimately draws the scar slightly below the surrounding skin level. This is often seen in surgical scars, which have divets or slight depressions in the center. Eversion prevents or at least minimizes this phenomenon by starting with slightly raised skin which lays flat after the universal process of contraction, which occurs at about 2-3 weeks after injury. The medical community generally recommends skin edge eversion to promote the least noticeable scar. Unfortunately, skin edge eversion is difficult to achieve with simple stitches or glues. More complex stitches that promote adequate eversion are time consuming to place and are used in less than one case in one hundred.

Currently, after sutures, staples, or other closure techniques, patients are often told to remove dressings within 48 hours, even though it is known that follow-on dressings can reduce scar formation. However, in an embodiment of the invention, the wound healing process is broken into three stages during which three different dressings can be applied. The first stage primarily requires a moist healing environment. A moisture-tight sealant is designed to reduce unwanted shock and promote a moist environment. The second stage, beginning 3-4 days following wound closure, often benefits from rich application of nutrients and oils. Vitamin E and other compounds can be contained within a soft dressing to promote healing and a refreshing feeling to the skin. The third stage begins 7-8 days following wound closure. Although the skin has largely healed at this point, there are still compounds that can reduce scarring. A combination of beneficial substances can be included within the third stage dressing to maximize scar softness and reduce discoloration.

After thorough cleaning of the wound edges, the wound closure components are affixed to the skin. For example, attachment processes for the closure components include adhesive backing, pre-placed skin glue, skin staple, or other adherent mechanism. Once applied to a skin edge, several techniques may be used to allow fine-tuning of placement of the closure components or their members, including but not limited to, sliding tracks on the attachment piece, a swivel element, such as for example a swivel element within the piece, or a replaceable adhesive back.

In various embodiments, the members of a wound closure component are placed opposite each other on either side of a surgical wound. They may be approximated (drawn together using connective elements), such as, for example, an interlocking system or other fastening device. When the components are brought into approximation, the attached portion of the wound should similarly close. In some embodiments, the closure should provide for as little space as possible between closure components and skin. In some embodiments, the release of the attached members should be possible, such as, for example, either through a protected release mechanism or through a release tool.

In some embodiments, components are placed in spaced relation, such as for example at intervals, along the long axis of the wound. These intervals can be long to allow drainage in wounds with high risk of infection or short for wounds which require a more controlled approximation. The intervals may be regular or irregular in length. All components may be placed and then the members connected (such as for example when the connective elements are engaged) to close the wound or the wound may be closed incrementally as each component pair of members is added.

In some embodiments, the coupled closure device (including both members when engaged) is about 5 mm in length and 3 mm in height (small size). In other embodiments, the coupled closure device is about 10 mm in length by about 5 mm in height (medium size). In further embodiments, the coupled closure device is about 30 mm in length by about 10 mm in height (large size). In various embodiments, the aspect ratio (length versus height) may range from approximately 1:1 to approximately 3:1. In some embodiments, the aspect ratio of a small closure device is about 1:1, and in additional embodiments, the aspect ratio of a medium and/or large closure device is about 3:1. In one embodiment, the aspect ratio is about 2:1.

Non-limiting examples of materials contemplated for the wound closure components include plastic, metal, polypropelene, high-density polypropelene, and other polymers or thermoplastic materials, or combinations thereof. In some embodiments the wound closure components are bioabsorbable. In one embodiment, the components will be light, strong, and waterproof. It is possible that with some materials, the components may be cleaned and sterilized for reuse. The components may be applied under sterile or medically clean conditions depending on the type of wound and according to the best judgment of the healthcare provider. In some embodiments, the components (or one or more members thereof) contain an agent, such as for example a chemical, to detect and signal impending infection. Alternatively, in some embodiments, such an agent, may be added to or above the closure during or after the procedure.

Such components can be manufactured using methods including but not limited to plastic injection molding or other technology known in the art. The use of identical members simplifies manufacturing.

In some embodiments, the components provide a vertical force orthogonal to the wound plane, thereby creating wound edge eversion to promote cosmetic healing. This may be accomplished through an upward curve of the skin-apposing surface of each member of each component, a system that mechanically raises the component undersurfaces when paired components are joined, or another mechanism. In some embodiments, the wound closure components are multiple, paired, independent, external, low-profile and provide skin edge eversion and tight paired locking. Some embodiments of the device are constructed so that there are four hinge points with each paired set. These hinge points can significantly contribute to proper skin eversion based on the geometry of the devices and the transfer of forces from a direction along the skin surface to a direction substantially orthogonal the skin surface.

Advantages of this device and method include, but are not limited to, the needleless technique, the ease of the technical procedure, the excellent skin edge apposition, the beneficial wound healing environment that is created, the efficacy possible for large wounds, and a high degree of patient comfort during and after the procedure.

In one embodiment, the wound closure component members may be easily placed and repositioned on the skin via a pressure sensitive adhesive bonding. These members may be set in appropriate position before releasing a second adhesive bonding agent that creates a long-term bond between the member and skin. For example, without limitation, a long-term tissue-bonding agent is cyanoacrylate. Other biological glues can also be used, such as, for example, thrombin gel.

In various embodiments the opposing members may interlock mechanically with a male-female latch. A single member may have both latches so that the male faces the female aspect when the members are set facing each other. In this way, the same member type may be used on both sides of the wound (they may be identical) and they will interlock with each other. The members may have a tapered edge, including but not limited to a beveled contact edge, so that the skin near the wound interface is raised mechanically upon attaching the closure components. In various embodiments, a long-term skin bonding agent may be released automatically upon connecting the opposing closure members; it may be released manually by the health care provider from a glue container (such as for example a dispenser) within the component, or it may be manually added and allowed to diffuse along the underside skin interface (between the first surface and the skin) of the closure member.

Various devices may be used to support easy and accurate placement of the wound closure components. One such device provides gross wound edge apposition. In one embodiment, this device is a temporary closure device, such as for example a deformable perimeter defining an opening. In some embodiments, this device has a pressure sensitive adhesive backing which can be manipulated and will hold its shape. In this way, once it is attached to skin around the wound, manipulation of the object will bring and hold skin edges (such as for example wound edges) in gross apposition. In one embodiment, the device is a plastic oval with an internal thick wire and an underside pressure sensitive adhesive. In another embodiment, the device is pressure sensitive adhesive handles which are placed on either side of the wound and allow a healthcare provider to use one hand to squeeze edges of the wound together. By way of non-limiting example, in some embodiments, two separate handles having pressure sensitive adhesive on at least one surface are placed with one handle on either side of the tissue opening before closing the opening. A healthcare provider can pull and/or push these handles together using a single hand, such as, for example, using the thumb and forefinger of one hand. Thus, gross apposition of the edges of the tissue opening can be achieved with one hand. Therefore, as one hand brings the edges of the tissue opening together, the other hand can be used to place a closure device, such as, for example, an adherence-based closure device, allowing a single healthcare provider to close a tissue opening with two hands. In another embodiment, a device supports placement of wound closure components once gross wound edge apposition has been attained. In some embodiments, this device allows closure components to be placed and releases a long-term skin bonding agent, such as for example cyanoacrylate, to create a semi-permanent bond.

In various embodiments, a single device may be used to provide gross wound apposition and to apply wound closure components. In some such embodiments, one element of the device brings skin edges into gross apposition. By way of a non-limiting example, this element may be pressure sensitive adhesive pads or other tacky or sticky pads which provide friction on the skin surface. In some embodiments, these pads may be mechanically controlled by the device to pull toward each other, bringing skin edges into gross apposition. In some embodiments, another element of the device allows fine-tuning and placement of wound closure components. Fine-tuning may be accomplished through mechanisms, including but not limited to, a mechanical roller switch or another mechanism. In various embodiments, placement of closure components may be accomplished by lowering a closure component having pressure sensitive adhesive backing onto skin over a grossly apposed wound. In one embodiment, another component of the device releases a long-term skin-bonding agent to create a semi-permanent bond between closure component and skin.

FIG. 1 depicts one embodiment of the invention, which includes two locking wedges. First member 1 contains an adhesive undersurface 5, in which an adhesive is attached to or on a first surface 5 of the member, to attach to the skin edge, and a male locking component 3, which is a connective element on a second surface 10 of the member substantially orthogonal to the first surface. The paired opposing member 2 contains female locking component 4 and adhesive undersurface 6.

The connective elements may differ in various embodiments. In some embodiments, the connective elements are interlocking and may comprise a locking mechanism. By way of a non-limiting example, the connective elements may include, but are not limited to, a ball in socket structure, hook and loop attachment, clasp, magnet, lace, ratchet, suture ligature, snap system, photobonded, non-photobonded, staple, resilient member (such as, for example, a spring), or other locking mechanism. In some embodiments, the connective elements are adhesives, including but not limited to, glue or tape. In one embodiment, the connective elements are a ball in socket structure due to the strong grasp and ease of closure of this type of mechanism. In some embodiments, the first member has a locking member extending outward from the second surface of the first mechanism, and the second component has a receiving member.

Adhesive undersurface 5, 6 may be a peel-to-expose adherent backing, a pressure sensitive adhesive, a rough surface that attaches to a glue-prepared skin edge, or another adherence mechanism. In some embodiments, at least one layer has positioned therein channels and/or perforations, or uses the inherent porosity of the materials, such that the layer is in communication with the first surface.

In some embodiments, the members comprise one or more layers, and at least one layer is a porous material. In additional such embodiments, the porous material holds the second adhesive, such as for example, cyanoacrylate. In addition, reservoirs for the second adhesive could also be used in conjunction with the porous material. In some embodiments, the second adhesive is dispensed intentionally as the connective elements become engaged or after the connective elements are engaged in the latching or locking step. In some embodiments, the second layer is sealed by a material that provides pressure-induced porosity. In additional embodiments, this layer is a selectively-permeable layer, which can control or regulate, among other things, the direction of flow of a material. In some embodiments, such a material is similar to a vapor barrier used in outdoor garments that allows moisture to travel in one direction.

Figure 2:
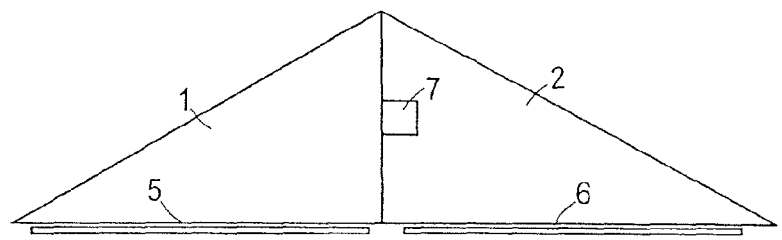
FIG. 2 is a schematic cross-section of a closure component in which the members are joined.

FIG. 2 shows the closure component of FIG. 1 in which the second surface of the first member has been brought in operative relation to the second surface of the second member such that the connective elements engage each other. In this embodiment, the joined members form a tight bond 7 and are shown forming a pyramidal low-profile shape.

Figure 3:
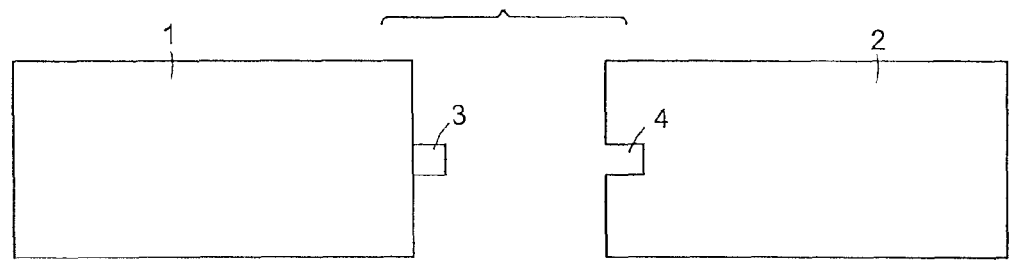
FIG. 3 is a schematic top view of a closure component.
Figure 4:
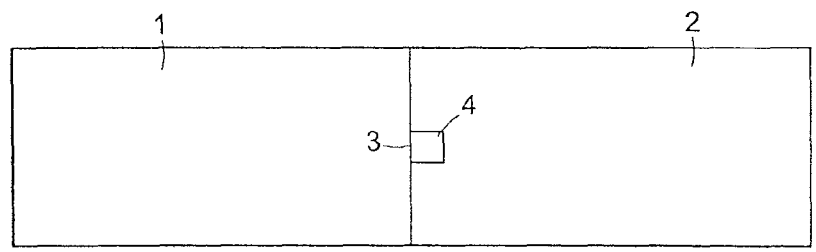
FIG. 4 is a schematic top view of a closure component in which the members are joined.

FIG. 3 depicts a top view of the closure components of the embodiment of FIG. 1. FIG. 4 shows a top view of the embodiment of FIG. 2 in which the closure members are joined by the connective elements.

Figure 5:
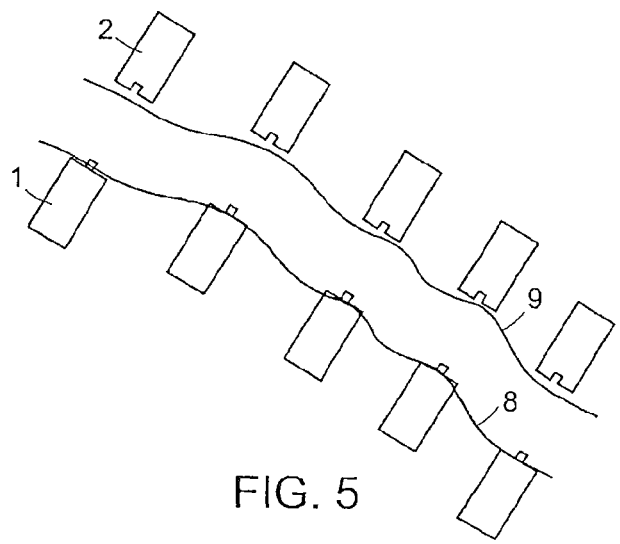
FIG. 5 is a schematic top view of multiple closure components placed at set intervals.

FIG. 5 shows a series of closure components. First member 1 is shown approximately opposite a second member 2, forming a pair. The pairs of closure components are shown placed at fixed intervals, which are of approximately equal length, along free skin edges 8, 9 of a wound. For small, complex tissue openings, the pairs of closure components can be positioned from about 0 to about 3 mm apart. For medium size tissue openings, the pairs of closure components can be positioned from about 0 to about 1 cm apart, and for large and/or complex tissue openings, the pairs of closure components can be positioned about 0 to about 5 cm apart along the edge of the tissue opening. In one embodiment, the interval length is about 3 mm.

Figure 6:
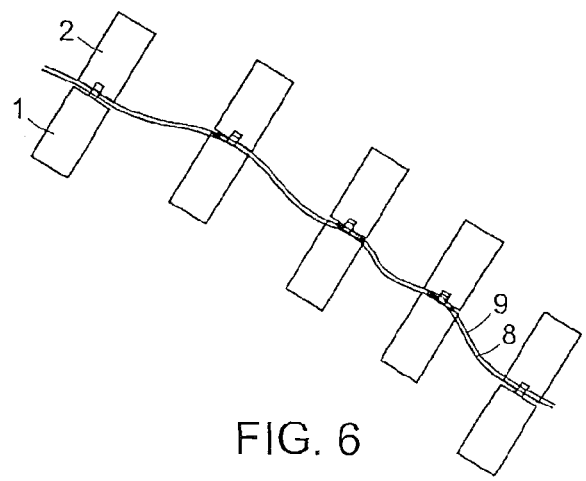
FIG. 6 is a schematic top view of multiple closure components placed at set intervals and in which the members are joined, bringing skin edges into apposition.

FIG. 6 depicts the series of closure components of FIG. 5 in which the paired members are joined to bring together skin edges into close apposition, promoting improved healing and reduced scarring. Each of the pairs of members has been brought in proximity to each other such that the connective elements are in operative relation and become engaged. This causes the underlying skin to be pressed together such that first wound edge 8 is brought in proximity to second wound edge 9. The paired members can either be joined as each pair is placed or after all components are placed along both edges of a wound at the discretion of a healthcare provider. It is understood herein that the mechanism for bringing the connective elements in operative relation and/or engaging them could be done manually by a healthcare provider, using a tool, such as, for example, a handheld tool using any other appropriate tool or instrument or using a combination thereof.

Figure 7:
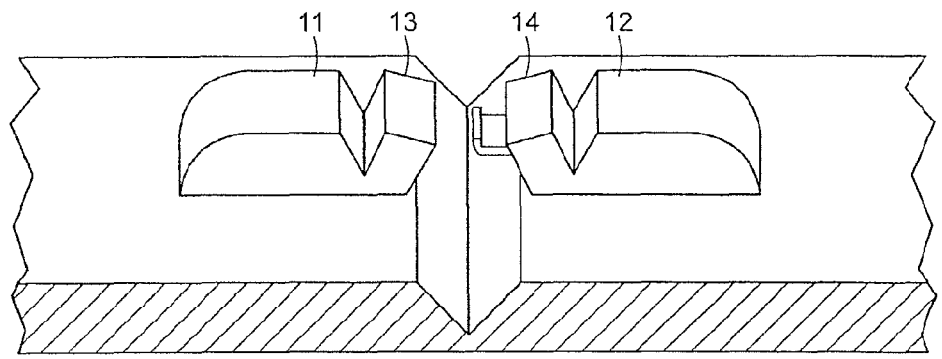
FIG. 7 is an oblique view of a closure component that provides mechanical closure and skin edge eversion.
Figure 8:
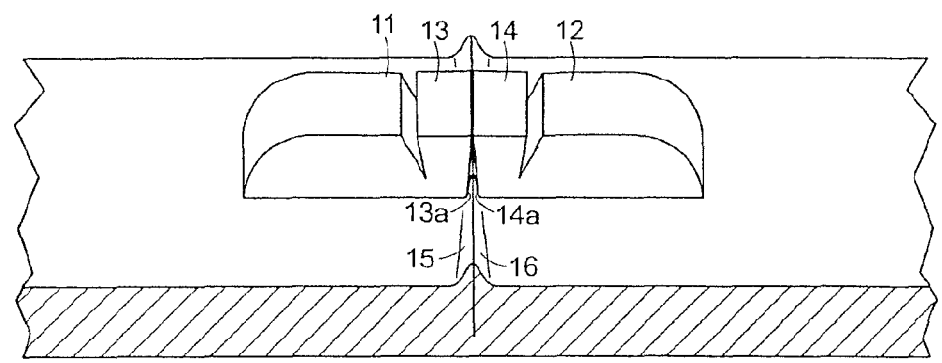
FIG. 8 is an oblique view of a closure component that demonstrates how closure can produce mechanical skin edge eversion.

FIG. 7 depicts one embodiment of the invention, which allows for mechanical locking of wound closure component members as well as mechanical skin edge eversion. Shown here, two beveled edges, upon apposition, will cause upward traction and create local edge eversion. In the depicted embodiment, cutaway sections 13, 14 of closure members 11, 12 facilitate tissue opening edge eversion. In this embodiment, cutaway sections 13, 14 provide a jointed or flexible device that allows the turning or pivoting of a part on a stationary frame, within each member. In some embodiments, the transition region is a hinge. In additional embodiments, the hinge is cut on a diagonal such that the angle between the plane defining the bottom surface and the surface having the connective elements is about 45°. When the connective elements become engaged, any movement, for example, upwardly, occurs within either or both members, resulting in the mechanical eversion of the tissue opening edges. Thus, the transitional region defined as a hinge is positioned such that beveled edges 13a, 14a of the closure device apply pressure by pressing against tissue adjacent to and/or at the edge of the tissue opening and force the tissue nearest the tissue opening edge upward when the connective elements become engaged to lock first member 11 to second member 12. In some embodiments, when the tissue closure device is used on the skin, both the epidermal and dermal layers are forced upwards to evert the tissue opening edges. As shown in FIG. 8, first member 11 and second member 12 are brought together such that the connective elements are in operative relation to each other. This forces beveled edges 13a, 14a to draw upward as the connective elements engage. This action simultaneously draws attached skin 15, 16 upward, resulting in eversion of the wound edge. As depicted in FIG. 8, cutaway sections 13, 14 have moved relative to their position in FIG. 7.

Figure 9A:
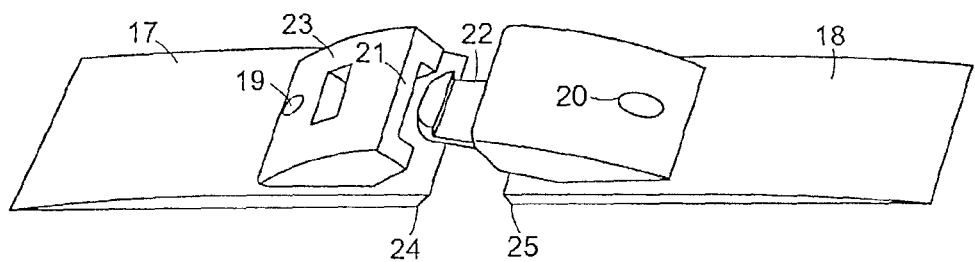
FIG. 9A is an oblique view of a closure component that provides mechanical closure, skin edge eversion, and latch release.
Figure 9B:
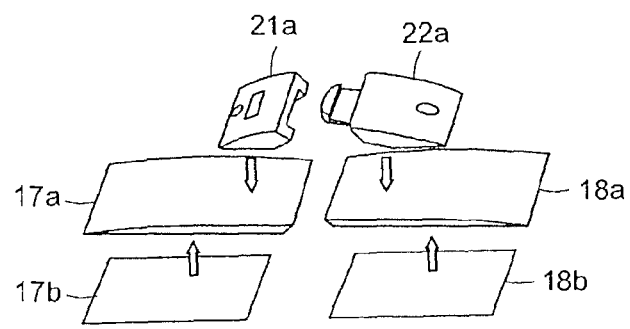
FIG. 9B is an exploded view of FIG. 9A.

FIG. 9A shows one embodiment of the invention, which allows for simple mechanical closure, mechanical skin edge eversion, and closure release through a push button release hole. The two members have bases 17, 18, which attach to skin at the undersurface (or first surface). The latch mechanism represented here shows female end (connective element) 21 juxtaposed near or in proximity to male end (connective element) 22. This embodiment also includes latch release (closure release mechanism) 23 to unlock the members. In some embodiments, the members may be unlocked and relocked by engaging the connective elements again. Also shown are holes 19, 20, which can be used for application of an adhesive. In some embodiments, a long-term skin-bonding agent is dropped or permitted to be released through these holes. In this embodiment, beveled edges 24, 25 are used to force mechanical skin edge eversion. FIG. 9B depicts an exploded view of an embodiment such as that shown in FIG. 9A. As illustrated in FIG. 9B, a component, in some embodiments, has layers: two members 21a, 22a (such as, for example, a plastic clip), elastomeric base 17a, 18a, and adhesive 17b, 18b such as, for example, a pressure sensitive adhesive coating.

FIG. 9B is an exploded via illustrating the components described with respect to FIG. 9A.

Figure 10:
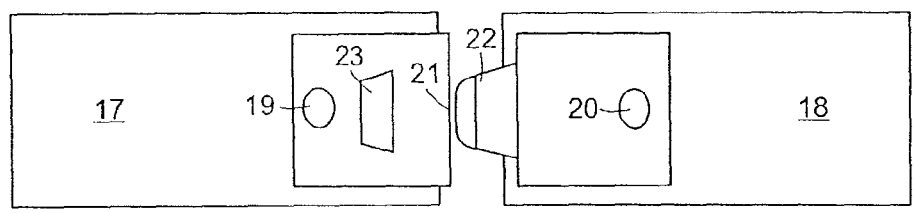
FIG. 10 is a top view of a closure component that provides mechanical closure, skin edge eversion, and latch release.
Figure 11:
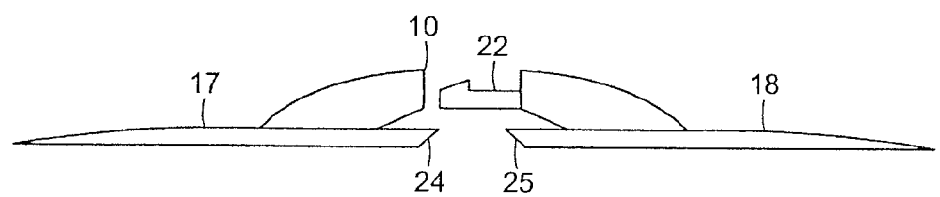
FIG. 11 is a lateral view of closure component members that provide mechanical closure, skin edge eversion, and latch release.

FIG. 10 shows a top view of the embodiment of FIG. 9A, and FIG. 11 shows a side view of the embodiment of FIG. 9A. Second surface 10 is not a flat surface in this embodiment. Beveled edges 24, 25 at the transitional region between first surface and second surface of the member is more clearly depicted in FIG. 11.

Figure 12:
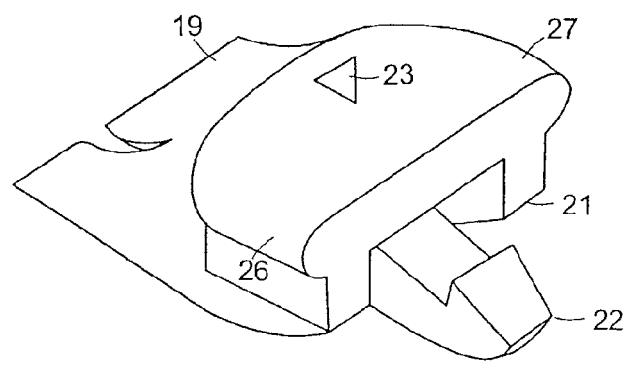
FIG. 12 is an oblique view of a wound closure component that provides mechanical closure, skin edge eversion, latch release, and allows for members to be the same on opposing sides of the wound.

FIG. 12 shows an alternate embodiment of the invention, which allows for simple mechanical closure, mechanical skin edge eversion, closure release, and design symmetry. In this embodiment, female latch mechanism 21 and male latch mechanism 22 are side by side on the same member. If a similar piece were placed on the opposite side of a wound, its conformation would be the mirror image of the opposing member, allowing for each male latch to interface with (or engage) the female latch on the opposing member. This eliminates the need for differently structured members on each side of the wound, allowing for greater ease of manufacture because all of the members are identical to the extent possible. The embodiment depicted here also contains wings 26, 27, or protrusions extending from the member. In some embodiments these protrusions are substantially parallel to the first surface. Such protrusions allow for easier handling. The embodiment depicted in FIG. 12 also includes hole 19 (an opening provided in plane that is substantially parallel to the first surface and spaced apart from the first surface extending through to the first surface) for introduction of an adhesive, such as for example, a second adhesive or semi-permanent bonding agent. This figure also depicts a latch release mechanism (closure release mechanism) 23, which can be used to disengage the first and second components. Disengaging the first and second members can be used, by way of a non-limiting example, to facilitate removal of the members after the wound has healed or to facilitate repositioning one or more of the members.

In some embodiments, the invention provides a device for closing and maintaining closed a cutaneous wound in order to promote healing, said device having a plurality of pairs of small independent members which can be placed on and bonded to opposing skin edges of a wound at set intervals; the paired members contain a mechanical locking process, allowing opposing members to be joined to bring skin edges into apposition within a specific section of the wound.

In additional embodiments, the device further includes an agent bonding the closure component to the skin, such as for example adhesive or glue. In further embodiments, the locking mechanism that attaches members at opposing edges of a wound is mechanical rather than adhesive. In some embodiments, the locking mechanism includes male and female pieces which join opposing members. In one embodiment, the locking mechanism includes a ball in socket structure.

In further embodiments, a sliding lock runs in a direction longitudinal to the wound axis and holds opposing wound members together. In additional embodiments, a release button or tool exists to release locked members. In some embodiments, the locking mechanism is reflexive, with the lock being symmetric along the long axis of the closure member, allowing for a single design to function on either side of the wound. In various embodiments, the components are narrow and low profile to limit obtrusiveness and risk of accidental dislodgement. In additional embodiments, the members have a fine-tuning placement mechanism allowing their position to be slightly altered once affixed to the skin, and in some such embodiments, the fine-tuning mechanism consists of a pressure sensitive adhesive undersurface which can be replaced until proper positioning is attained. In further embodiments, the fine-tuning mechanism consists of a small rail, ball bearing, or hinge allowing a degree of flexibility to the closure member before or after attachment to the opposing member. In additional embodiments, the flexible fine-tuning mechanism has an independent locking system so that once appropriately placed, the member can be made immobile.

In some embodiments, the independent locking system is mechanical. In additional embodiments, the independent locking system is a strong adhesive agent that prevents accidental removal.

In additional embodiments, a mechanism elevates the outer lip of the skin edge, producing wound edge eversion to improve cosmetic outcome. In some embodiments, the wound edges are elevated by adhering to an upwardly curving lip on the skin-apposing surface of the closure member. In further embodiments, the wound skin edges are elevated by member undersurfaces that raise mechanically when opposing members are locked together. In some embodiments, two beveled member edges brought into apposition mechanically force the undersurface of the closure member upward.

In further embodiments, a chemically impregnated material can be placed over a wound to recognize and signal an impending infection. In some embodiments, the chemical reagent which detects and signals impending infection is incorporated within a wound closure device. In additional embodiments, the chemical reagent which detects and signals impending infection is external, but made to integrate with or lay within or around the closure device.

Figure 13:
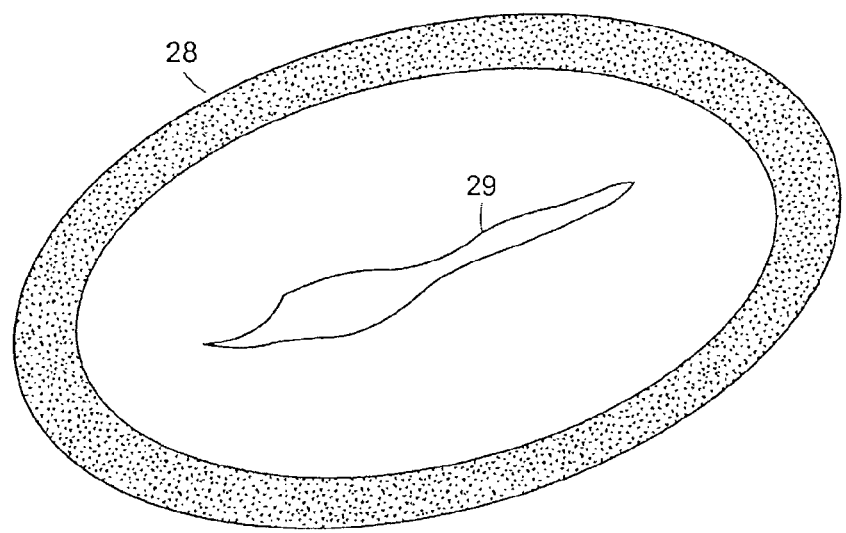
FIG. 13 is a view of a temporary closure device to achieve gross wound edge apposition, with a gaping laceration in its center.

FIG. 13 shows one embodiment of a compliant, temporary closure device of the invention, which is used to achieve gross wound apposition. In this embodiment, the device has deformable perimeter 28, which is oval in shape. The deformable perimeter defines an opening that surrounds wound 29. In some embodiments, the deformable perimeter also has at least one adhesive on at least one surface in contact with the tissue surface.

Figure 14:
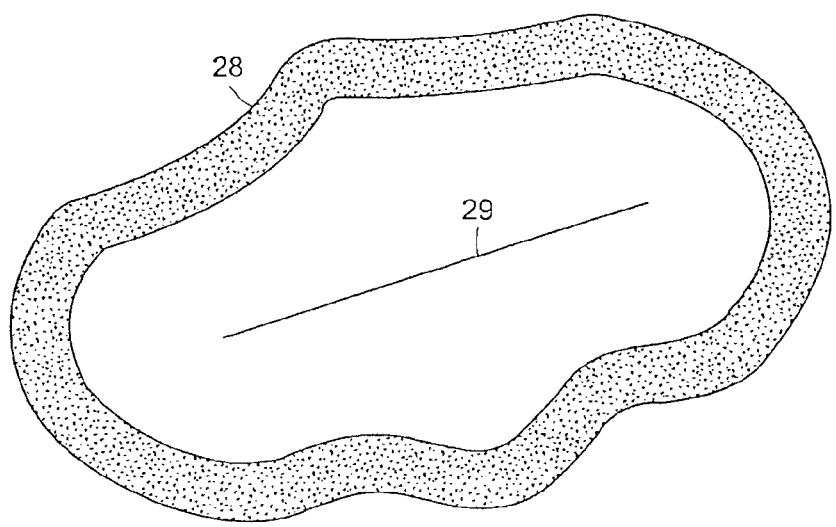
FIG. 14 is a view of a temporary closure device to achieve gross wound edge apposition, deployed so that the central laceration is grossly apposed.

FIG. 14 depicts the embodiment of FIG. 13 in which the deformable perimeter has been manipulated to close wound 29 by bringing the edges of the wound into proximity. The compliant perimeter in this embodiment maintains its shape after being manipulated in order to hold the edges of the wound closed.

In various embodiments, the invention provides device for achieving gross wound edge apposition having a control piece or control pieces which attach to the healthy skin around a wound through pressure sensitive adhesive at its undersurface and a mechanism to bring aspects of the control piece on either side of a wound together, thereby pushing the edges of the wound into apposition.

In some embodiments the control pieces are situated on either side of a wound and contain a single grip to allow easy holding or pushing. In various embodiments, the apposition mechanism is a healthcare provider gripping the pieces with opposing thumb and finger to squeeze them together.

In further embodiments, the control piece is a single oval which surrounds the wound. In additional embodiments, the oval holds its shape to maintain skin edge apposition once appropriately positioned. In some embodiments, the oval contains a thick wire within it to help it hold shape. In some embodiments, the apposition mechanism is a healthcare provider manipulating sections of the oval until skin edges are pushed toward each other into apposition.

Figure 15A:
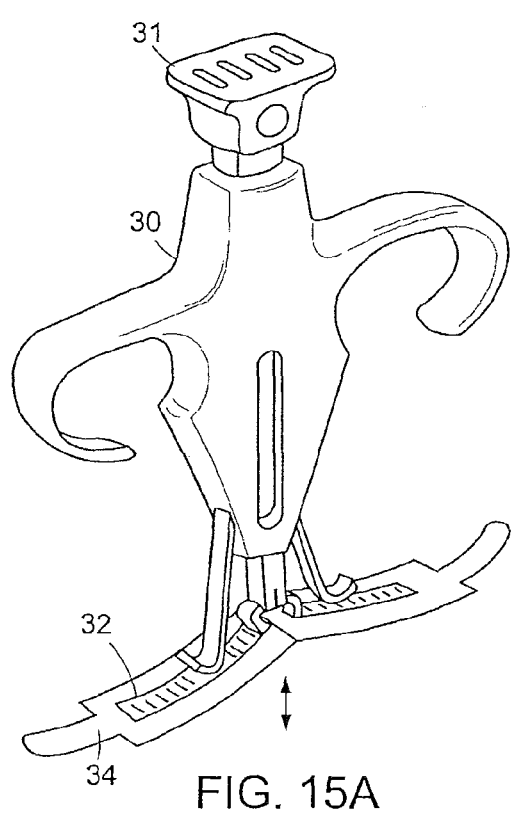
FIGS. 15A-15C are a representation of a device for applying closure components, assuming previous gross wound edge apposition, and an adhesive dispenser and a kit for use therewith.
Figure 15B:
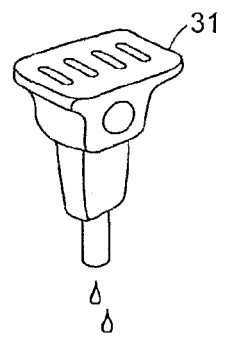
Figure 15C:
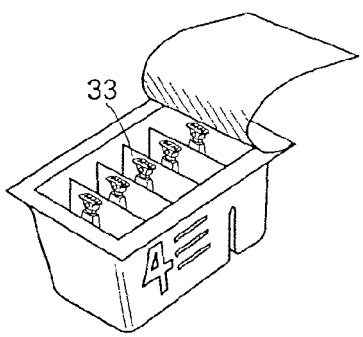

FIGS. 15A-15C illustrate an embodiment of the invention, which is a device that applies wound closure components. FIG. 15A shows one embodiment in which applicator device 30 contains a handle or handles to support easy grip. Applicator device 30 grips a version of a wound closure component 32, and contains plunger and reservoir mechanism 31 to release cyanoacrylate onto, into, or through closure component 32. In this embodiment, closure component 32 also contains peel-away backing (adhesive backing) 34. The plunger and reservoir mechanism 31 for dispensing cyanoacrylate is shown separately as a cyanoacrylate dispenser in FIG. 15B. Additionally, as shown in FIG. 15C, kit 33 may also be provided, which may contain additional closure components 33 for convenient retrieval and placement.

Figure 16B:
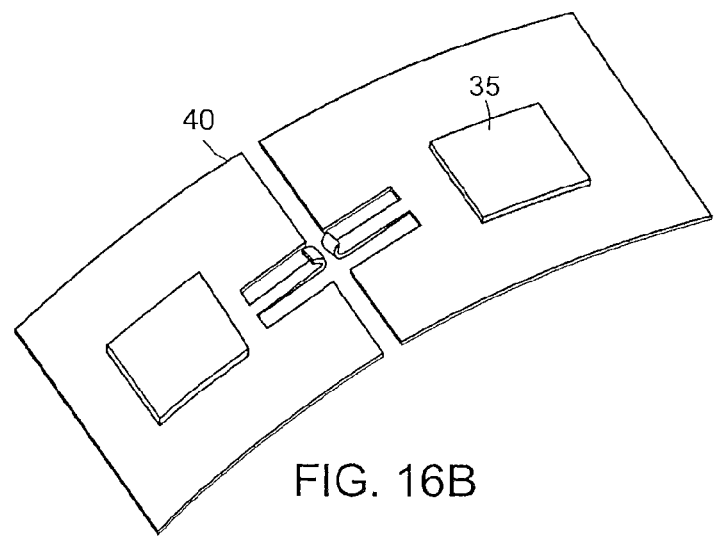
FIGS. 16A-16B are a representation of a device for applying closure components which does not require previous gross wound edge apposition and materials for use therewith.
Figure 16A:
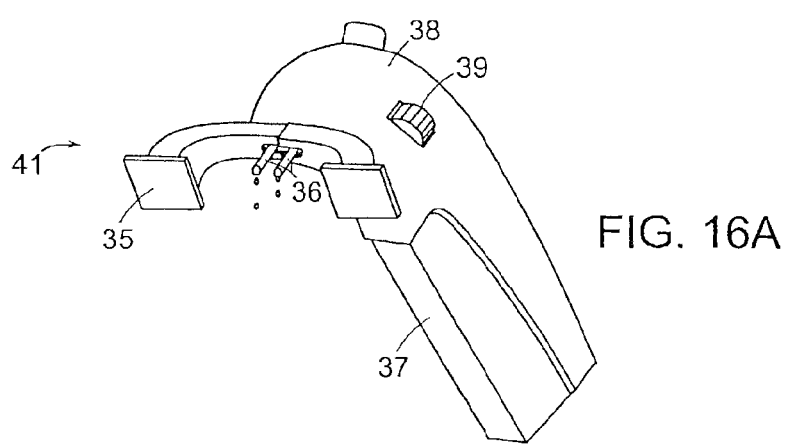

FIGS. 16A-16B illustrate one embodiment of the invention which includes placement device (or applicator device) 38, which provides gross wound apposition, wound closure component placement and fine tuning, and bonding agent release. One embodiment of applicator device 38 contains sticky pads 35 which can be placed on either side of the wound and brought together by squeezing grip 37 to achieve gross wound apposition. Once the skin edges are apposed, the placement of the wound closure component is fine tuned with a mechanical roller grip 39 until horizontal displacement is appropriate. In additional embodiments, displacement can be horizontal and/or vertical. When grip 37 is fully closed, the wound closure component is released on the skin of the wound. In some embodiments, this is accomplished using a release mechanism 36. A long term skin bonding agent may be released by the same mechanism. A kit shown in FIG. 16B containing closure components 40 may contain only the components or may also contain replaceable sticky pads 35 for the gross alignment process.

In various embodiments, the invention provides for a device for placing wound closure components having a mechanism to hold, lower, and release said closure components, and a mechanism to affix closure components in place. In some embodiments, the closure components are lowered with a hand grip. In further embodiments, the closure components are affixed with self contained pressure sensitive adhesives. In additional embodiments, an independent mechanism releases a long-term skin-bonding agent once the components are in place. In one embodiment, two sticky surfaces are placed on either side of the wound and mechanically drawn together to provide gross wound edge apposition prior to wound closure component placement. In some embodiments, the device allows fine-tuning of the closure component in the transverse and/or longitudinal direction prior to placement.

In further embodiments, the applicator device or other tool for use with the closure devices include one or more light-based guides (or mechanism for a light-based guide). In some embodiments, these guides are projected from the hand-held tools used for placing the device on the skin. In various embodiments, the light is produced in a pattern to aid the placement of the applicator device, tool, and/or closure component. By way of nonlimiting example, in some embodiments, one edge of the light pattern is cast on the edge of the tissue opening and the other edge of the light pattern is cast the appropriate distance from the wound for the edge of the device. In one embodiment, when the applicator device is positioned such that the light pattern aligns with the edge of the tissue, the applicator device is appropriately positioned for placement of the closure component. A further embodiment includes a mechanism for adjusting the light pattern based on the size of the closure component or other factors.

In some embodiments, a wound closure kit offers a systematic and appropriate layering of needed items to provide ease of use and improved step-appropriate sterility during closure. In various embodiments the kit may include at least one of an instruction layer, a cleaning layer, a sterile field layer, and a closure layer.

The instruction layer may include, by way of non-limiting example, a sturdy card with wound care instructions to be handed to the patient. This card would be sturdy, waterproof, of easy form to keep and provide reference, and provide suitable information regarding wound care, medical warning signs, and closure material removal. The card would be a timesaving technique for the provider and a mnemonic for the patient.

The cleaning layer may offer, by way of non-limiting example, a watertight cup to hold saline and a non-splash syringe to draw up saline and flush the wound. The layer may offer an option of access from outside the kit through a peel-away external cover so that fluid can be introduced into one section before the entire kit is opened and exposed.

The cleaning layer may be pulled off the kit to reveal a sterile field layer, which may include, by way of non-limiting example, sterile gloves on top and a sterile field below to allow the set up of a sterile procedure.

At the appropriate time in the procedure, the closure layer may be exposed. The closure layer contains, by way of non-limiting example, the wound closure system. This area may include one or more of the above-described components or another closure device or system.

In some embodiments, there may be no need for a sterile layer and the wound closure may be carried out under clean but not sterile conditions.

Advantages of the described kit include, but are not limited to, the ability to set up the entire kit including, without limitation, to added fluids and other substances in advance, clean and independent layers for each part of the wound closure procedure, and appropriate containment and display of instruments needed for each aspect of the procedure. Aspects of the procedure taken into account by the kit include, but are not limited to, those generally neglected by other kits, such as for example patient instruction, thorough wound irrigation, the need to lay out substances before donning sterile gloves, and an effective final wound dressing.

Figure 17A:
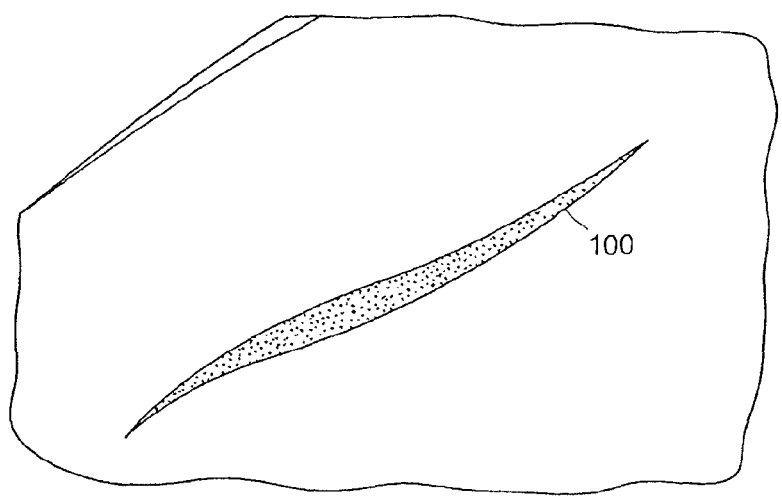
Figure 17B:
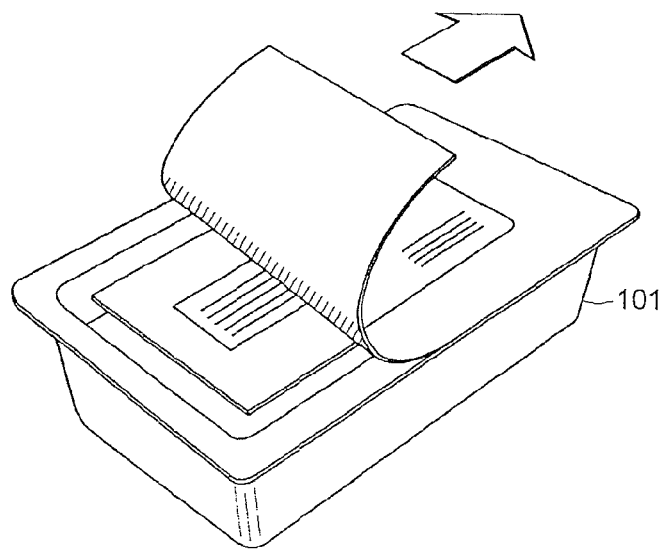
Figure 17C:
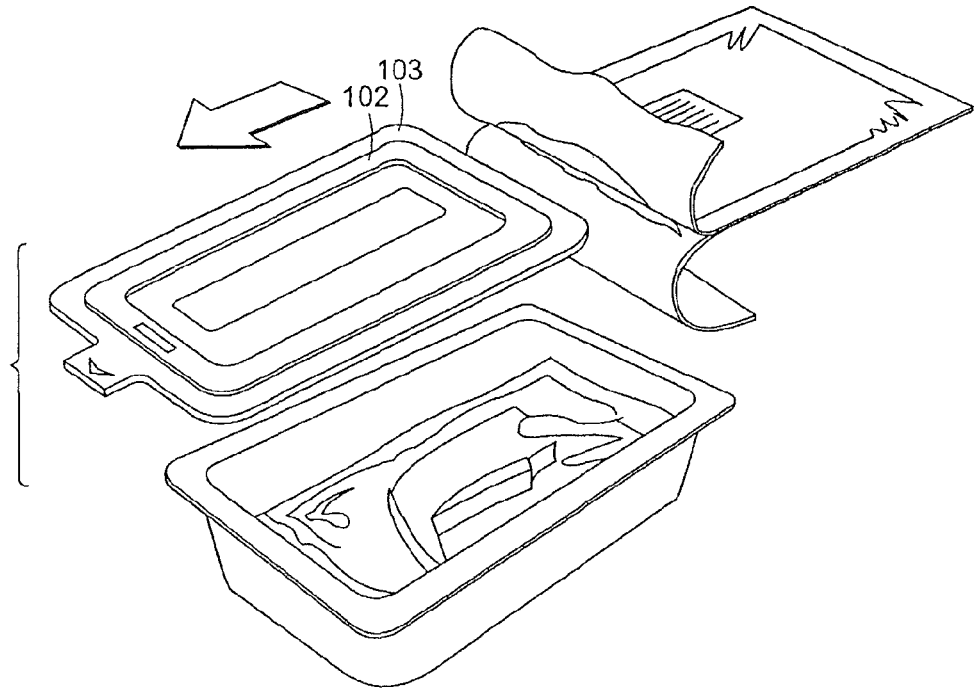
Figure 17D:
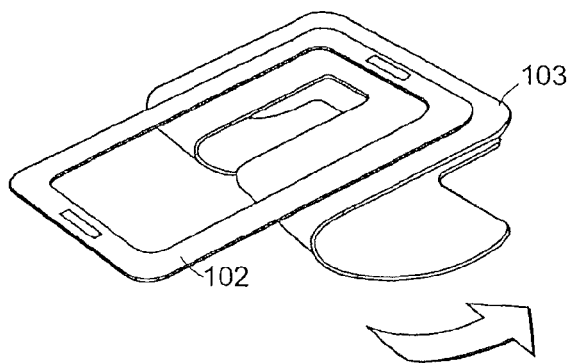
Figure 17E:
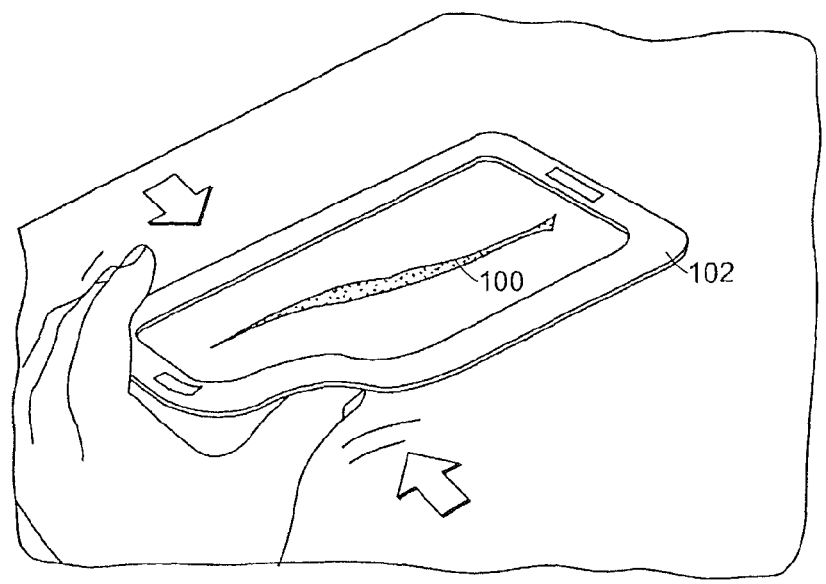
Figure 17F:
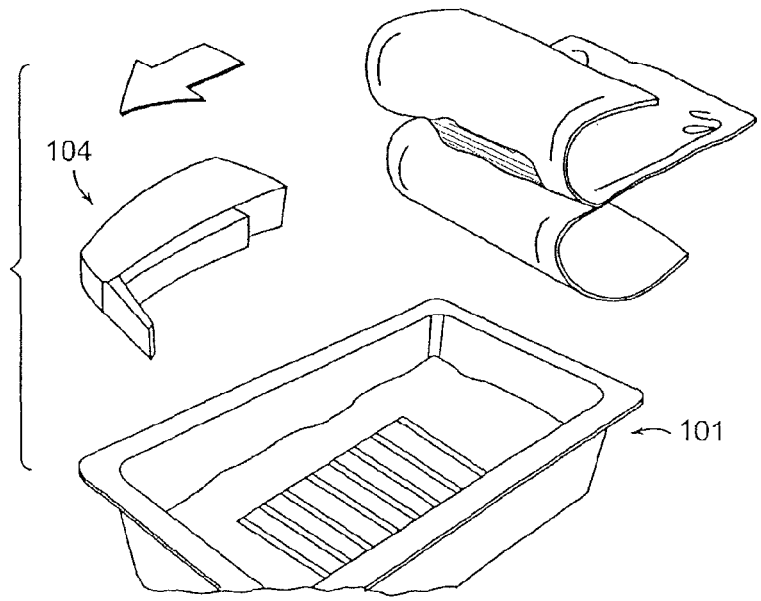
Figure 17G:
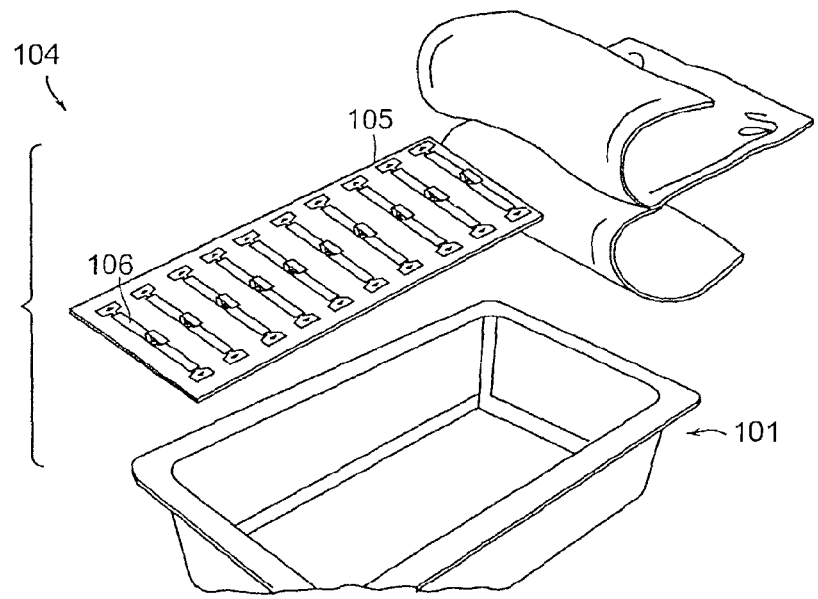
Figure 17H:
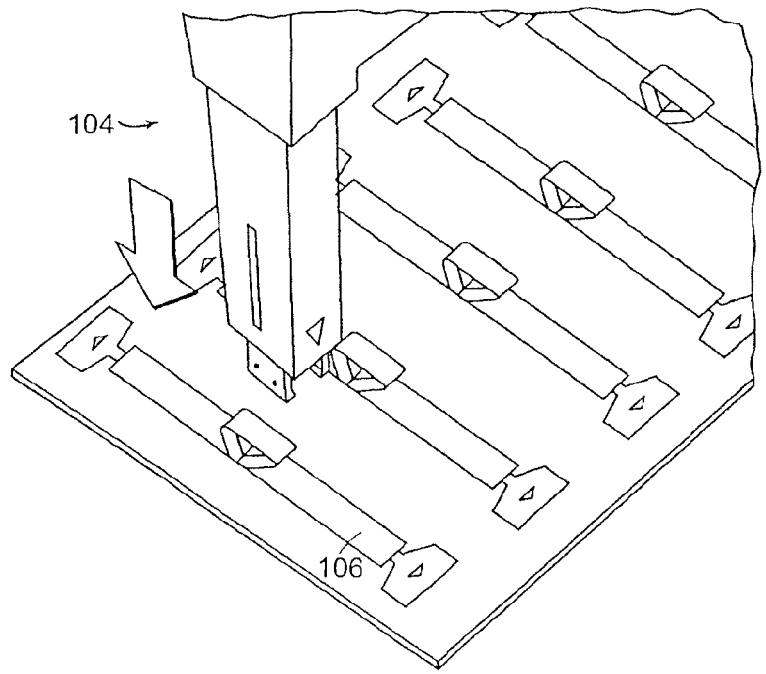
Figure 17I:
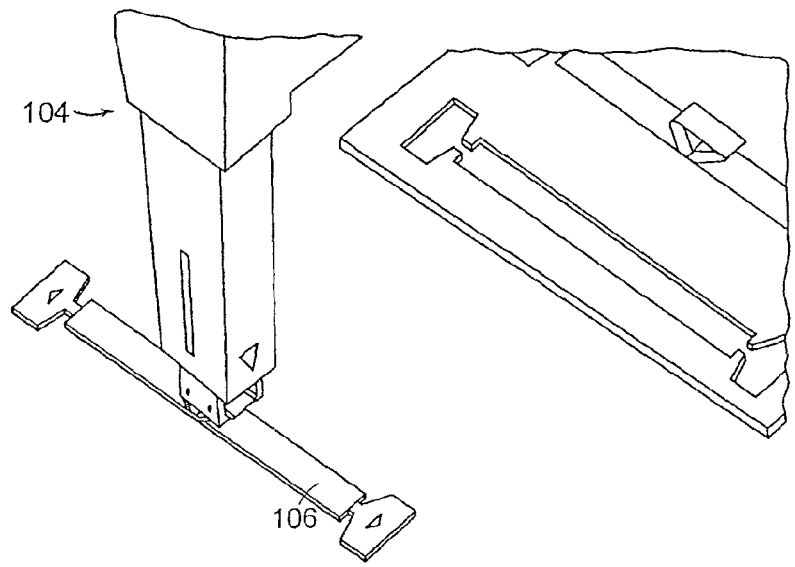
Figure 17J:
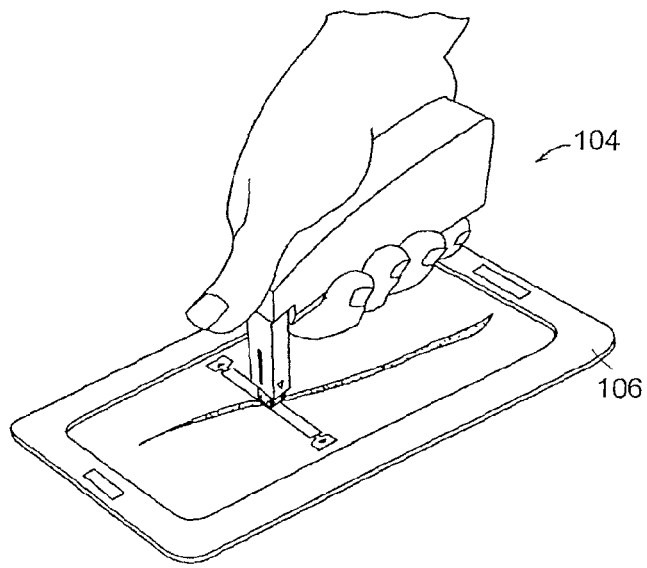
Figure 17M:
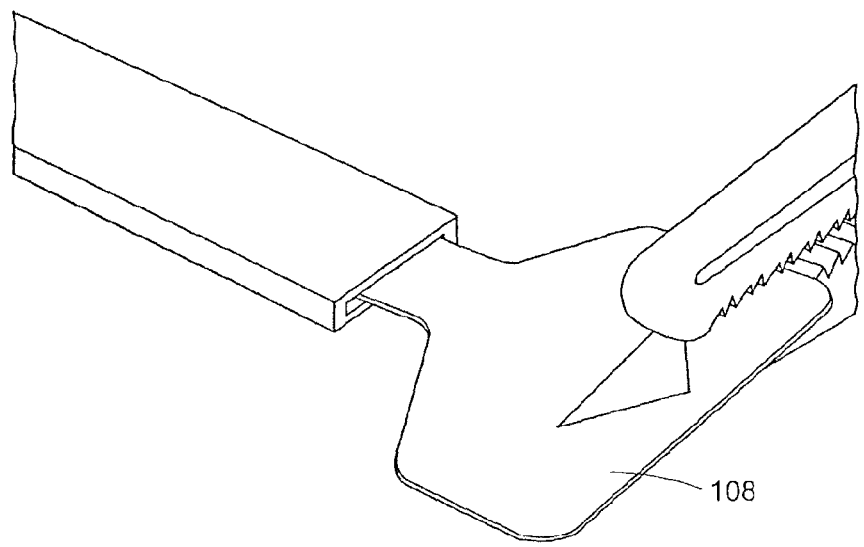

FIGS. 17A-17M illustrate a method using a kit for a wound closure system including the kit, various components contained within the kit, and a method of its use. FIG. 17A shows wound 100. The doctor or health care provider inspects and cleans the wound. In FIG. 17B the doctor opens kit 101 for closing a tissue opening by removing a cover from the kit. In this embodiment, the kit is a wound closure kit box. FIG. 17C depicts the removal of temporary closure device 102 (such as for example a flexure loop) from an individual sealed pack. Temporary closure device 102 is shown with pressure sensitive adhesive backing 103. In FIG. 17D, adhesive backing 103 is removed from temporary closure device 102 exposing the pressure sensitive adhesive. The doctor may remove part or all of the pressure sensitive adhesive backing. The doctor adheres the temporary closure device to a tissue surface around a tissue opening, which is depicted in FIG. 17E as wound 100 in a skin surface, and bends the temporary closure device to approximately close wound 100. The doctor then removes applicator device 104, which in the embodiment depicted in FIG. 17F is a handheld setting tool, from an individual sealed pack in kit 101. As shown in FIG. 17G, the doctor also removes multiple closure pack 105 (such as for example a multiple clasp pack) from an individual sealed wrapper which was in kit 101. In this embodiment, multiple closure pack 105 contains multiple closure components 106. FIG. 17H shows applicator device 104 being loaded with first closure component 106 such that a first single-piece clasp is being loaded into the hand tool. FIG. 17I shows the doctor using application device 104 (hand tool) to carry the clasp just over the approximate center of the laceration. As shown in FIG. 17J, the doctor uses applicator device 104 to adhere clasp 106 to both sides of the wound opening. After confirming satisfactory placement of the clasp to both sides of the wound opening, the doctor pulls trigger 107 of hand tool 104, which sets the clasp spring to evert the wound edge and close the wound as shown in FIG. 17K. FIG. 17L shows the placed closure component with the wound closed and eversion of the wound edge. As depicted in this embodiment, the closure component includes bridging member 109 and pull mechanism 108 (depicted in this embodiment as breakaway pull tabs). The doctor inspects the closure and eversion of the wound edge. If necessary, the doctor can peel up and remove the entire clasp assembly to start again with the process shown in FIG. 17H. If the placement and closure making the "stitch" is satisfactory, the steps shown in FIGS. 17H-17L can be repeated as needed to close the wound. After inspecting all the "stitches" confirming proper placement of the closure components, closure of the wound, and eversion of the wound edge, the doctor pulls out breakaway cyanoacrylate pull-tabs 108 to semi-permanently adhere the clasp assemblies to the skin.

Various embodiments of the invention provide for a method of closing and promoting healing of a wound without use of stitches, staples, or strips, said method including the steps of positioning elevated wound closure members on opposing edges of a skin wound; fine-tuning the position of each opposing closure member to allow for optimal wound apposition; and locking the opposing members in place before or immediately after bringing together a portion of the skin wound.

In some embodiments of the method, opposing wound closure components are placed at set intervals along the longitudinal axis of a wound. In additional embodiments, the intervals can be wide with large gaps to allow wound drainage or can be narrow with small gaps to improve skin edge apposition. In further embodiments, opposing wound closure members are fixed to the skin using adhesive material or glue. In some embodiments, a short-term adhesive agent provides holding strength during initial member placement and a long-term adhesive agent provides long-term bonding. In additional embodiments, the long-term bonding agent is contained and released from within the closure member to provide easier application.

Various embodiments of the invention provide for a device for improving the process of wound closure in the form of a kit offering step-appropriate cleanliness or sterility and easier to use working surfaces, having an instruction layer available on opening the kit, with a durable card of wound care instructions to be given to the patient; a cleaning layer containing non-sterile gloves, syringe and splash prevention mechanism to help the health care provider clean the wound; and a wound closure layer containing closure components and kept separate until the wound area is prepared for closure.

In some embodiments, all or some layers are physically separated. In various embodiments, a sterile field layer may be included for wound closure techniques requiring sterility. In additional embodiments, layers subsequent to the sterile field layer are sterile.

In further embodiments, a mechanism exists for introducing fluid or other substance into a specific portion of the kit in advance of starting the procedure. In some embodiments, a portion of the outside of the kit is covered by a removable barrier, which, when opened, creates a window to a specific layer of the kit. In additional embodiments, the removable barrier creates a window to a section of one layer, which contains an independent tub or container to keep a substance or fluid separated from the rest of the layer and kit. In some embodiments, the container within the layer is waterproof and can be used for sterile water, local anesthetic, or other substance or medication.

Figure 18A:
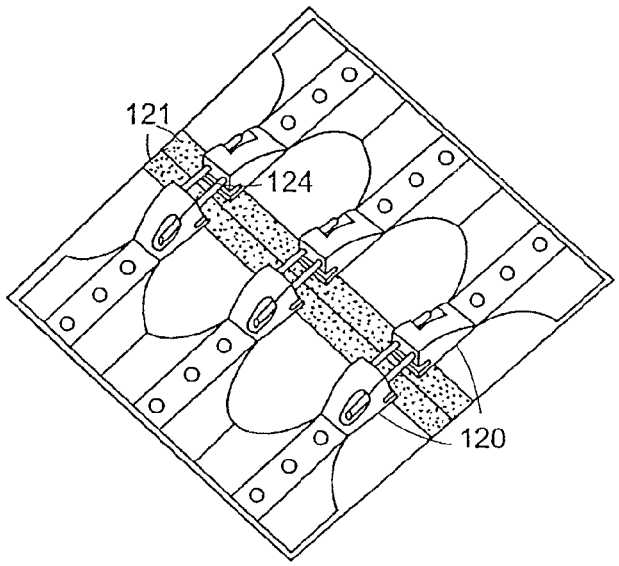
FIGS. 18A-18D are representations of a closure device containing multiple wound closure components and a method of its use.
Figure 18B:
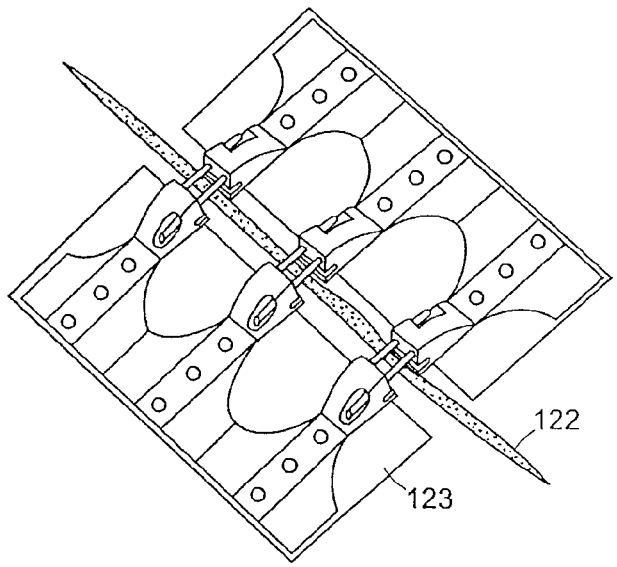
Figure 18C:
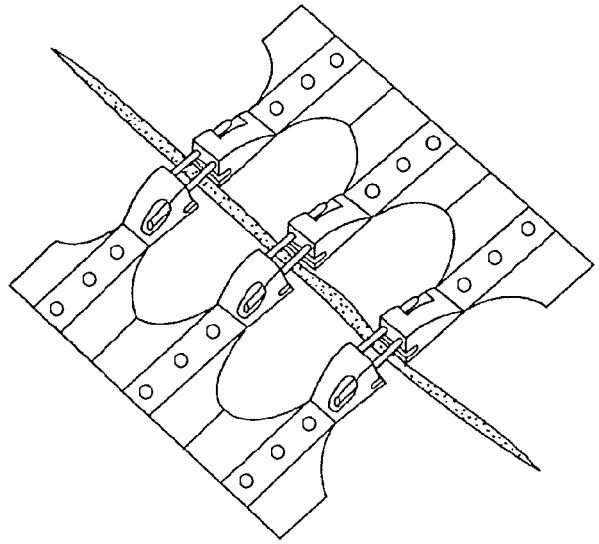
Figure 18D:
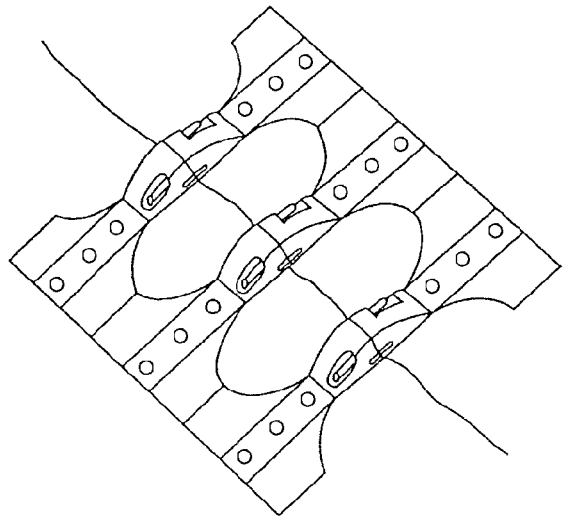

FIGS. 18A-18D show a wound closure device containing multiple closure components and a method of its use. In this embodiment, the doctor can use perforations to adjust the number of closure components 120 based upon wound length (such as, for example, one, two or three closure components) as shown in FIG. 18A. The entire device in this embodiment is backed with a pressure sensitive adhesive and a backing that peels away. The backing for shaded center portion 121 is peeled away first. The device in this embodiment is pre-adjusted for width (which in some embodiments is facilitated using bridging element 124) so that the device edges line up with the wound edges when the device is placed over wound 122 such that one member of each closure component is on one side of wound 122 and the second member of each closure component is on the other side of wound 122 as shown in FIG. 18B. The remaining backing 123 is removed. FIG. 18C shows the device after the removal of the remaining backing. The device is placed across the wound as described above in its slackened state. Another device, such as for example a disposable plastic tool, can be used to grip the components and bring the two members of each component together. (In some embodiments, a doctor or health care provider can manually do this as well.) When this is done, the two members of each closure component ratchet together applying equal tension to both sides of the wound in this embodiment. When this is completed, the wound edges are apposed, and the wound is closed. This is shown in FIG. 18D. The edges of the wound, the central portion, are everted. In this embodiment, cyanoacrylate is released internally.

Figure 19A:
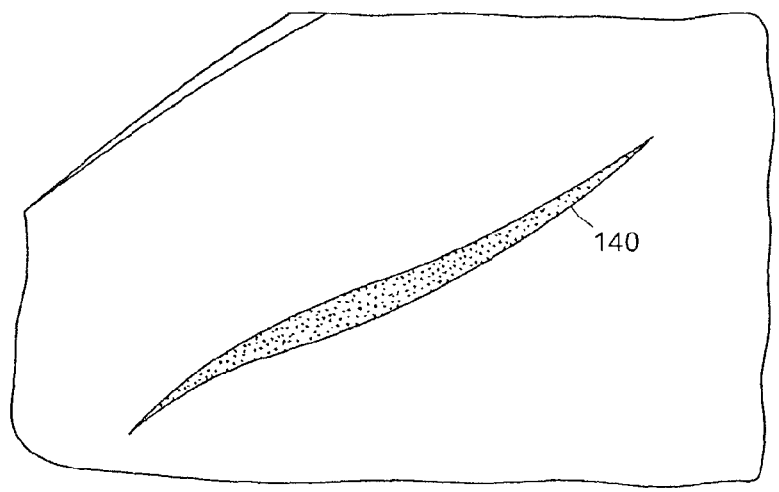
Figure 19B:
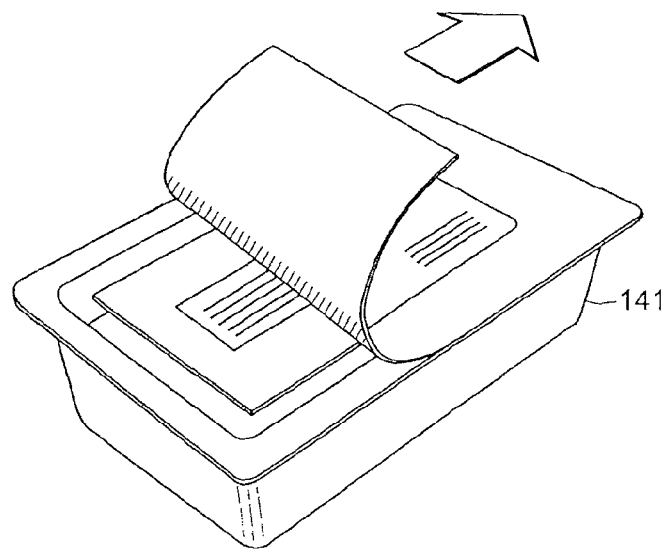
Figure 19C:
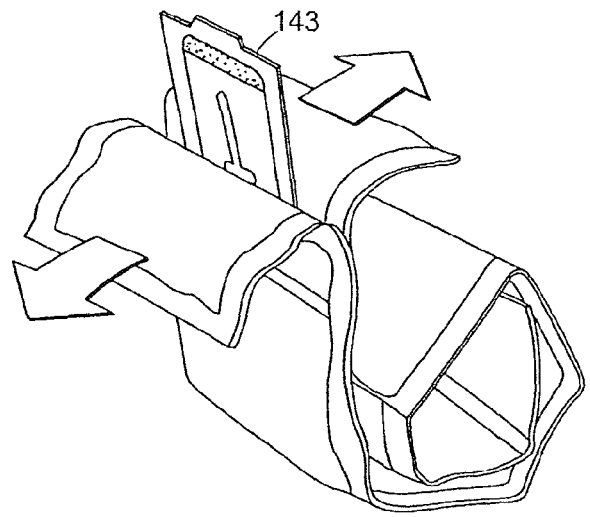
Figure 19D:
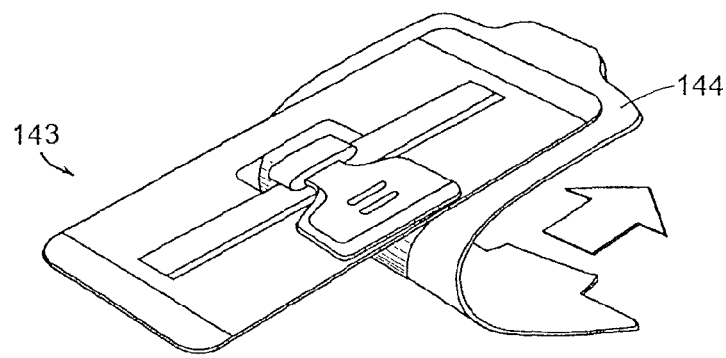
Figure 19G:
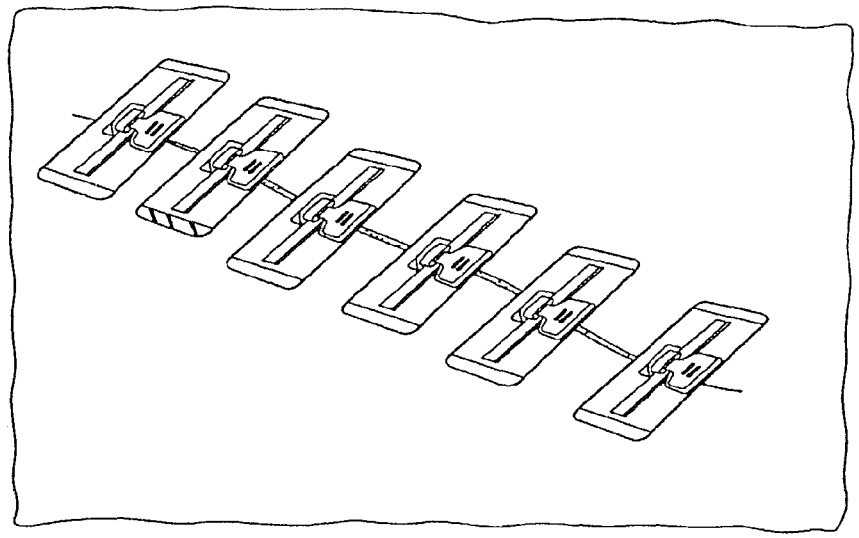
Figure 19H:
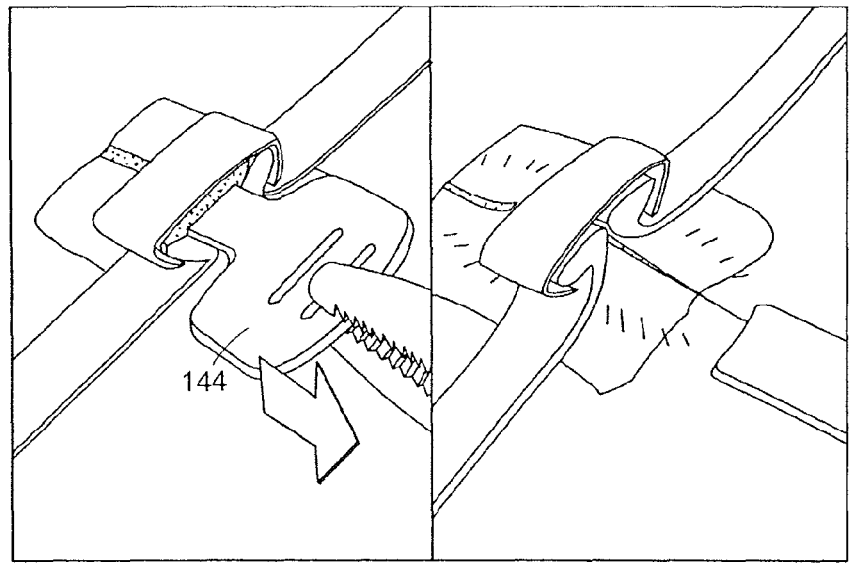
Figure 19I:
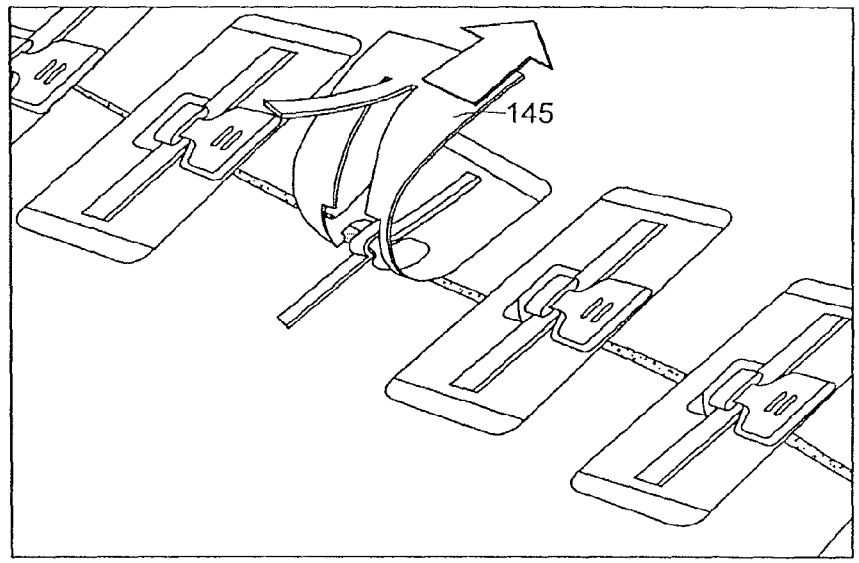

FIGS. 19A-19I show a method using a kit for a closure system including the kit, various components contained within the kit, and a method of its use. FIG. 19A shows wound 140. The doctor or healthcare provider inspects and cleans the wound. In FIG. 19B the doctor opens kit 141 for closing a tissue opening by removing a cover from the kit. In this embodiment, the kit is a wound closure kit box. As shown in FIG. 19C, individual closure component 143, such as for example a clasp pair in this embodiment, is removed from an individually sealed clasp-dispensing roll. The doctor removes pressure sensitive adhesive back strip 144 from closure component 143, as shown in FIG. 19D. FIG. 19E shows the doctor adhering the closure component to one side of the wound approximately halfway along the wound. The doctor can use one hand to push an unadhered side of the wound while pulling the adhered side with the second hand until closure and alignment of the wound is achieved as shown in FIG. 19F. The doctor then adheres the second side of the clasp-pair closure component to the other side of the wound and inspects placement and alignment of the closure component. If unsatisfied, the doctor can peel back either side of the closure component for repositioning and reapplying. These steps are repeated until the entire wound is aligned and closed satisfactorily as shown in FIG. 19G. FIG. 19H shows the doctor pulling out central clasp-pair tab 144 to activate eversion of the wound edge and final closure for each clasp-pair closure component. The doctor may then inspect the wound for final alignment, closure and eversion. Finally, as shown in FIG. 19I, the doctor peels up and removes an outer adhered area for each clasp pair closure component, which activates the dispensing of cyanoacrylate to both sides of the clasp, semi-permanently adhering the clasp-pair to the skin.

Figure 20A:
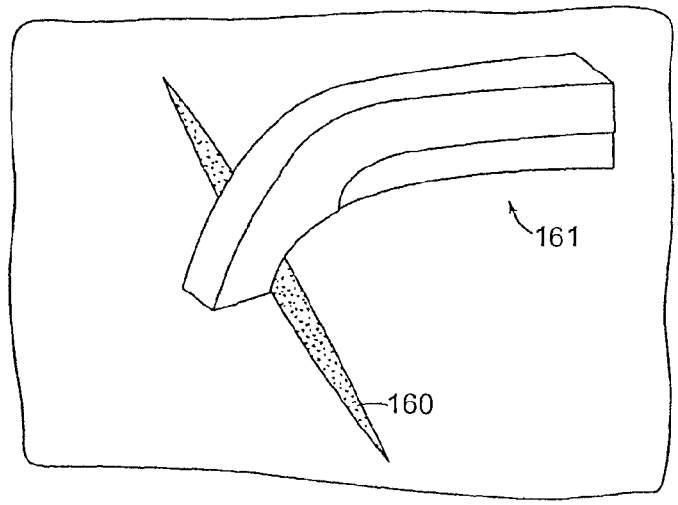
Figure 20B:
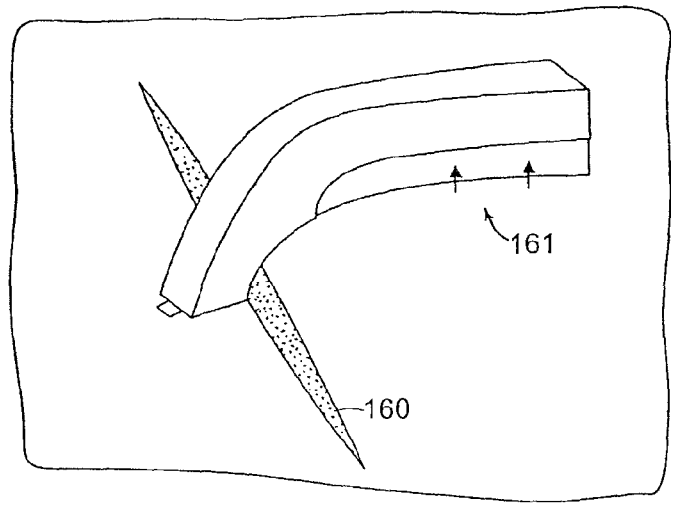

FIGS. 20A-20F show a wound closure device containing multiple pairs of wound closure components and a method of its use. In the embodiment depicted in these figures, the doctor uses hand tool 161, which is aligned with respect to wound 160 such that the inner edge of tool 161 is aligned with the wound edge as shown in FIG. 20A. This provides for alignment of the center of a closure strip over the wound edge. Thus, in this embodiment, the closure device is one piece, such as for example, a thick strip having a mechanism for mechanical eversion and a mechanism for internal release of a second adhesive. The doctor squeezes the trigger of hand tool 161 to release the edge of a closure strip and lays the edge on the skin as shown in FIG. 20B. A pressure sensitive adhesive under the closure strip adheres to the skin. In various embodiments, as the strip is pulled out of the placement tool, it passes between roller balls or another mechanism, squeezing the closure strip. This pressure breaks internal reservoirs containing a second adhesive, such as for example, cyanoacrylate bags in the closure strip, and flattens the internal plastic that will ultimately create eversion of the skin at the wound edge. The closure strip pulls the wound closed and a mechanism, for example, a firing tool, releases the final edge of the closure strip. In some embodiments, manual pressure or other mechanism may be used to facilitate wound closure. FIG. 20C shows the release of the closure strip from the hand tool. FIG. 20D shows the closure strip after it has been placed (deployed or applied). The doctor can then inspect the alignment and remove the strip if the placement or the wound closure is unsatisfactory. In some embodiments, the closure strip itself is composed of at least two layers, such as for example thin pieces of foam tape or neoprene, one on top of another. In one embodiment, the total thickness of the two layers is about 1.5 mm to about 3 mm. As shown in FIG. 20E, between these two layers are two reservoirs 163, such as for example bags, (one for each side of the wound), which in some embodiments are filled with an adhesive, such as for example, cyanoacrylate. Thus, one reservoir can be on each side of the tissue opening. In some embodiments, the reservoirs are about 0.5 mm thick when filled and do not add substantially to the overall thickness of the device. In other embodiments, more cyanoacrylate is used, and the total thickness of the device is about 2.5 mm to about 3 mm. Also between these two layers is a plastic eversion piece (eversion element) 164 in the middle of the strip. In various embodiments, these bags are broken as they are released through the placement tool, as discussed above, and cyanoacrylate slowly wicks through the undersurface of the foam tape to form a final bond securing the closure strip to the skin. After release from the placement tool, the eversion piece, which sits at the center of the strip, is no longer stretched flat as it was while passing through the tool. Thus, upon application (when placed or deployed), it returns to its relaxed arched position, bringing the wound edge into eversion as shown in FIG. 20F.

In some embodiments, the second layer is a porous material. In additional such embodiments, the porous material holds the second adhesive, such as for example, cyanoacrylate. Thus, the reservoirs for the second adhesive may not be present; however, such reservoirs could also be used in conjunction with the porous material. In some embodiments, the second adhesive is dispensed intentionally using pressure. In some embodiments, the second layer is sealed by a material that provides pressure-induced porosity. In additional embodiments, this layer is a selectively-permeable layer, which can control, among other things, the direction of flow of a material.

Figure 21:
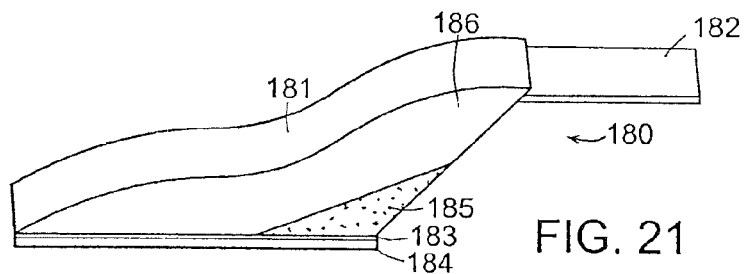
FIG. 21 is a schematic view of a male member.

FIG. 21 is a schematic view of male member 180 of an embodiment. In this embodiment, through-holes 181 provide access to apply additional material, including but not limited to glue-dissolving agents.

Figure 22:
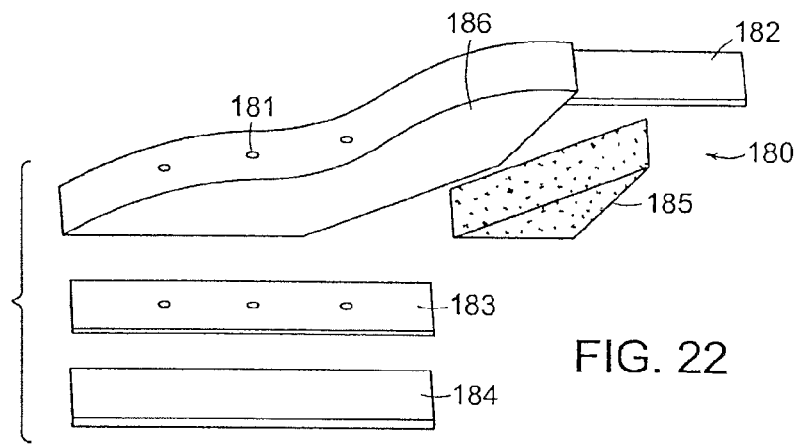
FIG. 22 is an exploded view of FIG. 21.

FIG. 22 is an exploded view of FIG. 21. This exploded embodiment of the design for male member 180 shows sponge layer 183 that provides the adhesive dispensing mechanism to the lower pressure sensitive adhesive layer 184. Wedge 185 illustrates a hard material (such as, for example, plastic) that ensures edge eversion. Upper body 186 is comprised of a flexible (softer) material (such as, for example, a polymer) allowing flexibility to accommodate movement and swelling, while not sacrificing adhesion strength. FIGS. 21 and 22 illustrate an alternative male latching mechanism (connective element) 182 that allows fine adjustment to placement errors, such as, for example, to correct minor placement errors.

In some embodiments, second layer 183 is a porous material. In additional such embodiments, the porous material holds the second adhesive, such as for example, cyanoacrylate. In addition, reservoirs for the second adhesive could also be used in conjunction with the porous material. In some embodiments, the second adhesive is dispensed intentionally as the connective elements become engaged or after the connective elements are engaged in the latching step. In some embodiments, the second layer is sealed by a material that provides pressure-induced porosity. In additional embodiments, this layer is a selectively-permeable layer, which can control or regulate, among other things, the direction of flow of a material.

In some embodiments, one or more of the members have one or more holes through all but the bottom layer (such as for example the "through-holes" discussed above), which in some embodiments comprises the first adhesive. In various embodiments, such holes can be used for application of various materials, including but not limited to a dissolving agent, to the interior of the surface that is affixed to the skin. In additional embodiments, the hole, which forms a channel, is sealed against the flow of the second adhesive. This can prevent or at least minimize diffusion of materials introduced through the channel to other parts of the member. Sealing the channel against the flow of the second adhesive helps to maximize the effectiveness of applying other materials through this aperture.

Figure 23:
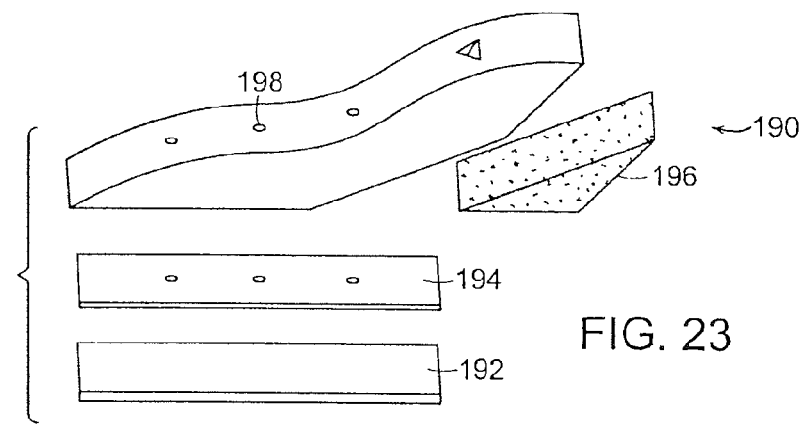
FIG. 23 is an exploded view of a female member.
Figure 24:
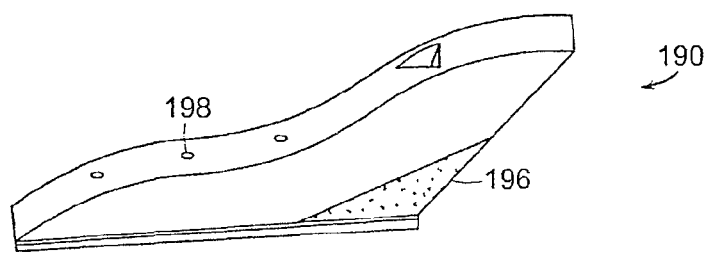
FIG. 24 is a schematic view of a female member.

FIG. 23 is an exploded view of a female member 190 corresponding to the male member depicted in FIGS. 21 and 22. FIG. 24 is a schematic view of a female member corresponding to the male member depicted in FIGS. 21 and 22.

Figure 25:
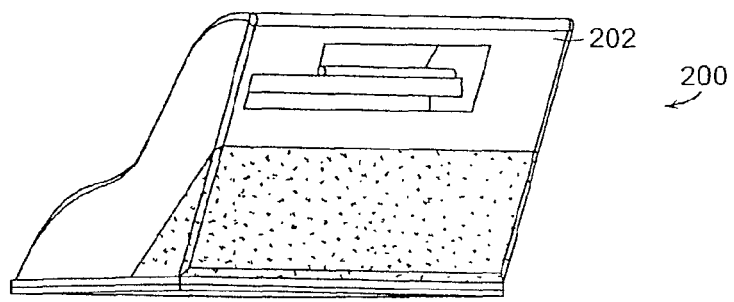
FIG. 25 is a schematic view of a female member showing a latching mechanism.
Figure 26:
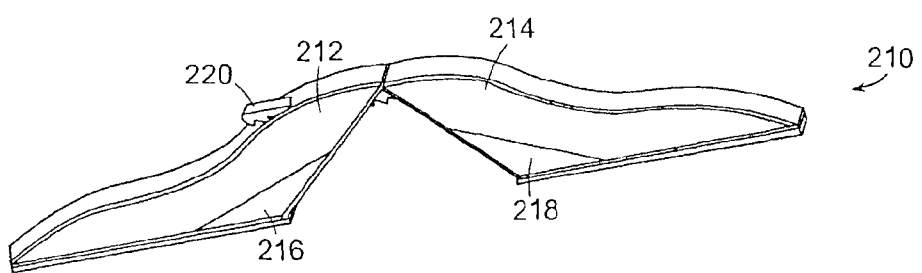
FIG. 26 is a schematic view of a male member and a female member with showing a latching mechanism.

FIG. 25 is a schematic view of a female member 200, such as, for example, shown in FIGS. 23 and 24, showing a latching mechanism 202. In one such embodiment the latching mechanism 202 is provided by a cantilevered extrusion. FIG. 26 is a schematic view of a male member 214 and a female member 212 fully engaged. In the embodiment depicted in FIG. 26, the male and female members are engaged at the limit of the fine adjustment mechanism 220, which in some embodiments could be extended to allow additional space between the male and female member to facilitate adjusting for incorrect placement of either or both components.

FIGS. 27A-27F are views of an embodiment of the invention, which allows for mechanical locking of one or more wound closure component members as well as mechanical skin eversion. This embodiment includes one member closure component, or in the alternative it can also include a closure component having two members. FIGS. 27A, 27C, 27D, and 27F illustrate views of the embodiment in an open state before being applied to a wound and closed. FIGS. 27B and 27E illustrate views of the embodiment in the closed position after being applied to a wound and closed. The closure components of this embodiment are closed by pulling on the balanced, opposing pull-tabs 270. Referring to FIG. 27A, the right pull-tab 270b is attached to the left base member 272 and the left pull-tab 270a is attached to the right base member 274. Thus, when the two pull-tabs 270a, 270b are pulled away from each other, the two base members 272, 274 are pulled toward each other into close apposition that promotes improved healing and reduced scarring. The locking mechanism is not shown in FIGS. 27A-27F. This embodiment uses placement of the pull tabs or the components that provide for hinges to create substantially orthogonal pressure on the skin and thus evert the skin edges when the closure components are closed.

FIGS. 28A-28D are different views of an embodiment of the invention which allows for mechanical locking of a wound closure component as well as mechanical skin eversion. These figures specifically illustrate three simple mechanical closures, any of which could be used to lock the embodiment of FIGS. 28A-28F or other embodiments. FIG. 28A illustrates a mechanical locking mechanism that uses interlocking overhangs 281 and underhangs 282 to close and lock the member into position as the skin edges are brought together into close apposition that promotes improved healing and reduced scarring. FIG. 28B shows a similar locking mechanism that uses male conical ends 283 that are inserted and mechanically locked into female openings 284. FIG. 28C is a pronated oblique view of a reversible ball and slot locking mechanism. The diameter of ball 285 is greater than the width of slot 286. Upon closure, ball 285 deflects slot 286 open to allow ball 285 to enter slot 286. After ball 285 passes through slot 286, slots 286 returns to near its original width and ball 285 is mechanically locked into slot 286, mechanically everting the skin edges. FIG. 28D is a profile view of the reversible ball and slot locking mechanism of FIG. 28C.

Figure 29:
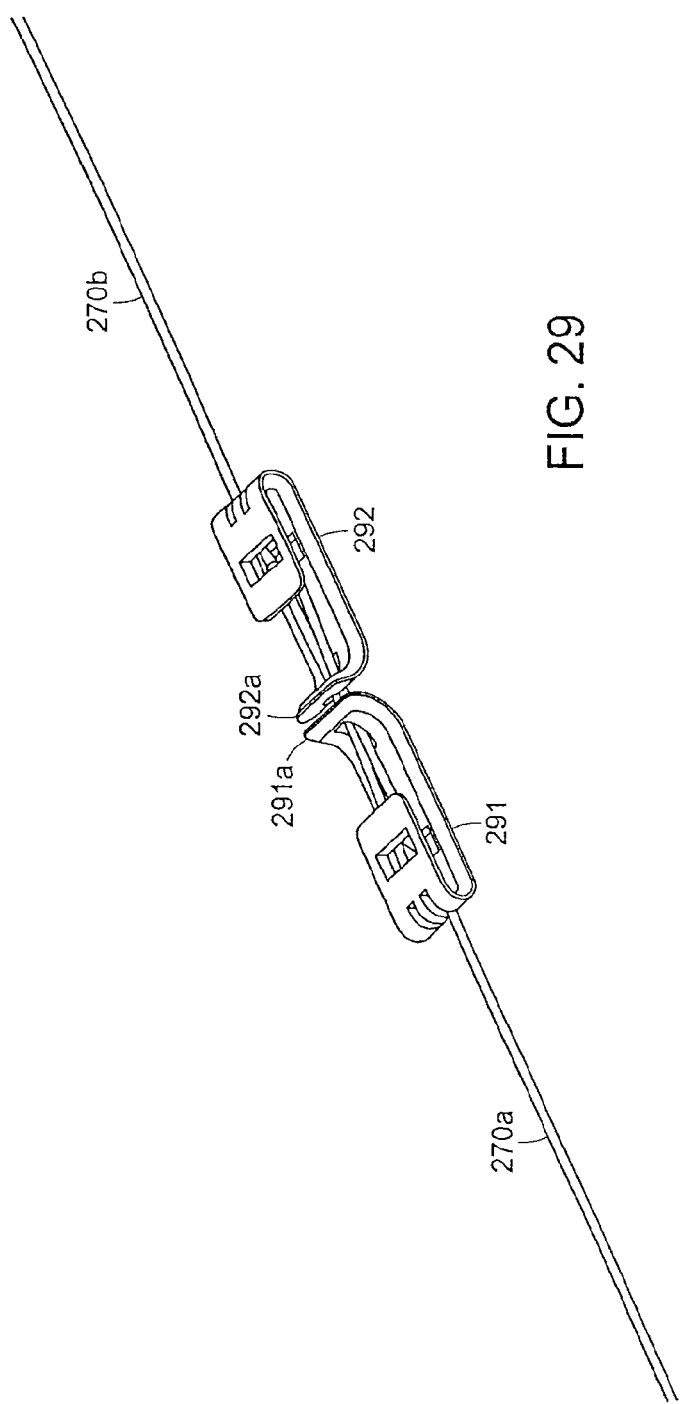
FIG. 29 is a schematic view of another embodiment of the invention that allows for skin eversion.

FIG. 29 illustrates another embodiment of the invention that allows for mechanical skin eversion. The closure components have a small, low profile above the surface of the skin, and also use balanced, opposing pull-tabs. This embodiment is made up of two wound closure component members 291, 292 and two pull-tabs 270a, 270b. Pull-tab 270a on left member 291 extends through contact points 291a, 292a of both members and through member 292. Pull-tab 270b on right member 292 extends through contact points 291a, 292a of both members and through member 291. Contact points 291a, 292a are upwardly-curved deformable elements. As the members of this embodiment 291, 292 are closed using pull-tabs 270a, 270b, contact points 291a, 292a become engaged and move in a direction substantially orthogonal to the skin surface, causing upward traction and creating local edge eversion.

Figure 30:
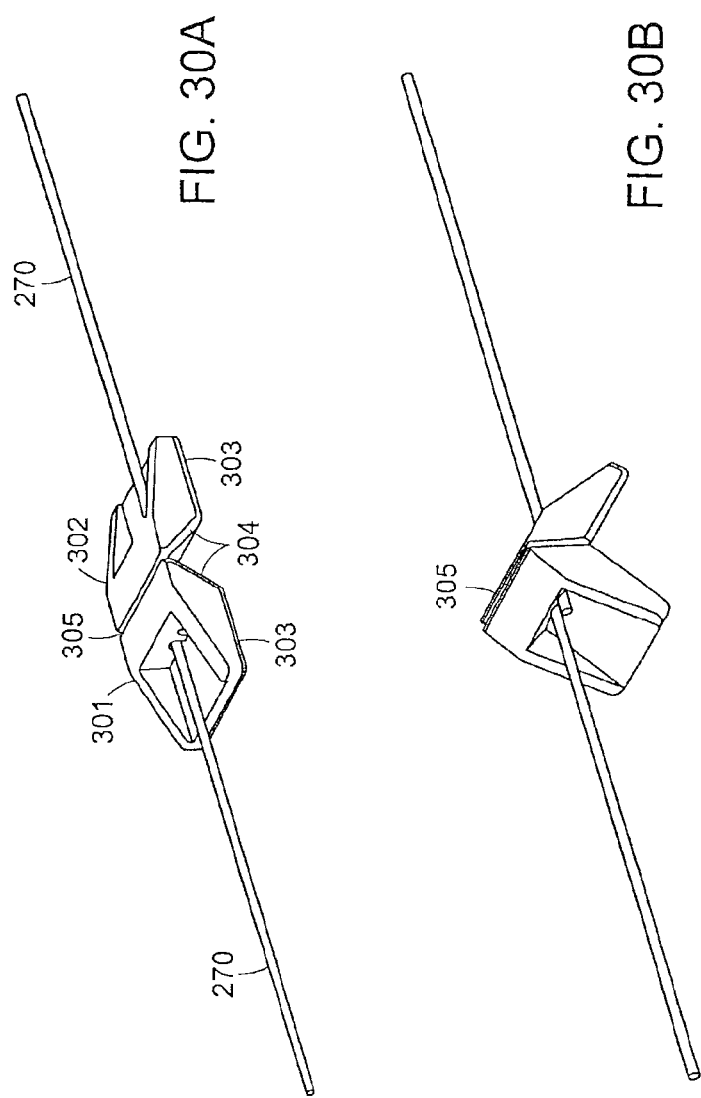
FIGS. 30A-30B illustrate views of closure components according to another embodiment that allows for skin eversion.

FIGS. 30A and 30B illustrate another embodiment of the invention that produces substantially uniform eversion. Members 301, 302 contain adhesive undersurfaces 303, on which an adhesive is attached to fix members 301, 302 to the skin edge. Second surfaces 304 angle up from adhesive undersurfaces 303. When adhesive undersurfaces 303 of each member are attached to the skin and members 301, 302 are pulled together via pull-tabs 270, top portion 305 of members 301, 302 make contact with each other first, as illustrated in the FIG. 30A. As the pull-tabs continue to be pulled after contact of the top portions 305, each member pivots around the point of contact. FIG. 30B shows the mechanically locked position of the members, in which second surfaces 304 are substantially flush with each other, and where the edges of the skin attached to adhesive undersufaces 303 has been mechanically everted, thus causing upward traction of the edge of the wound and creating local edge eversion.

Figure 31:
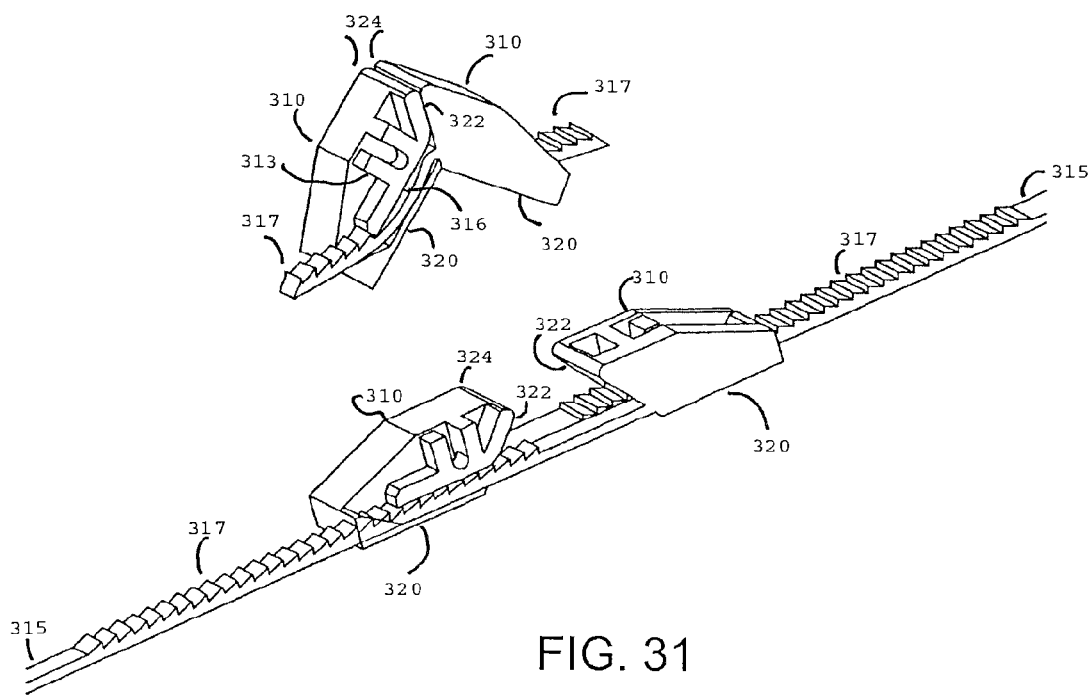
FIGS. 31-41 illustrate closure components according to another embodiment having ratchet mechanisms having a plurality of teeth to align, engage and lock the closure components.
Figure 32:
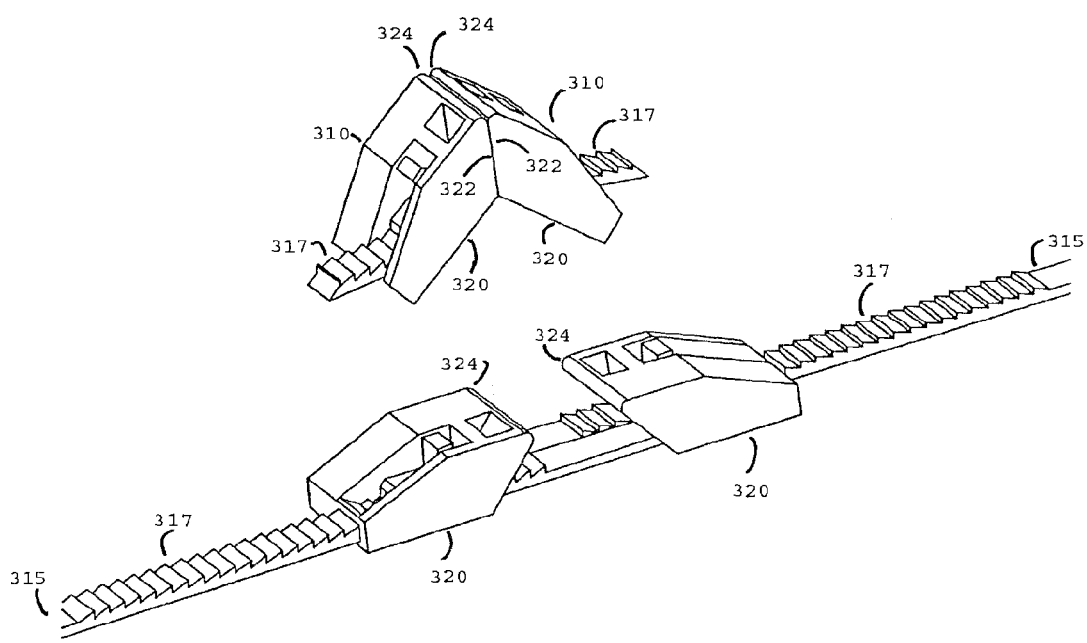
Figure 33:
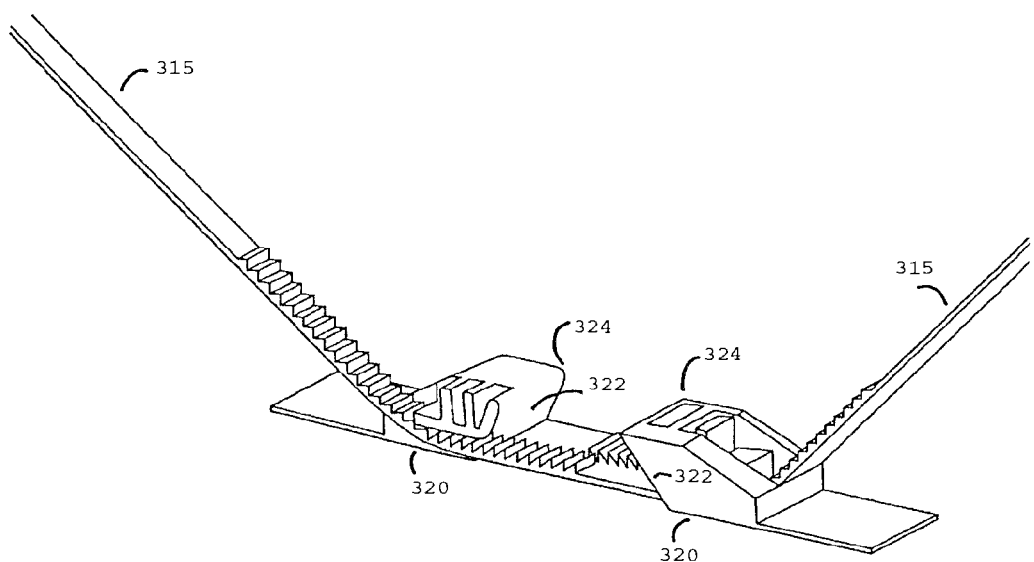
Figure 34A:
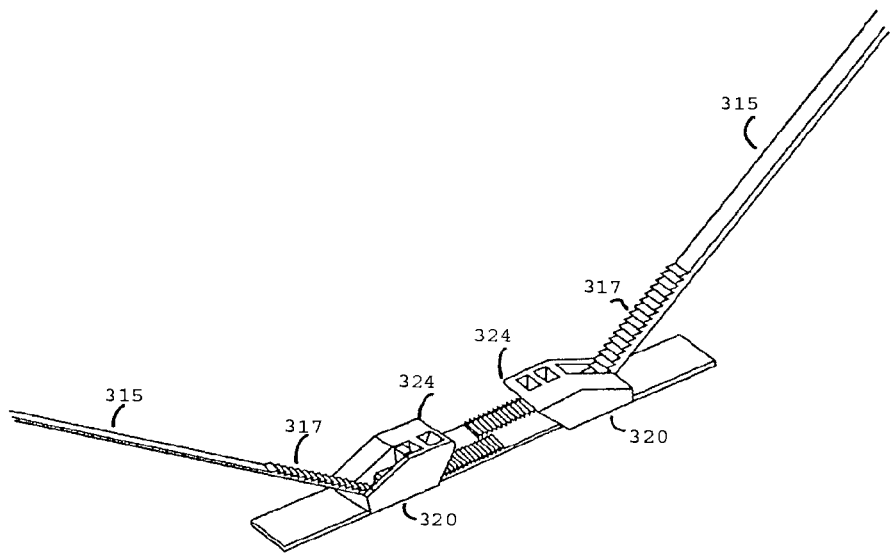
Figure 34B:
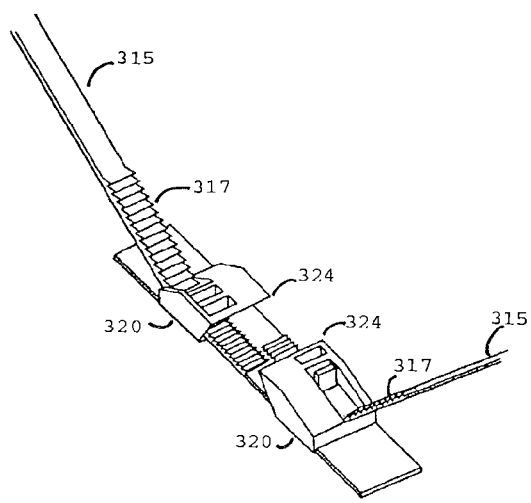
Figure 35:
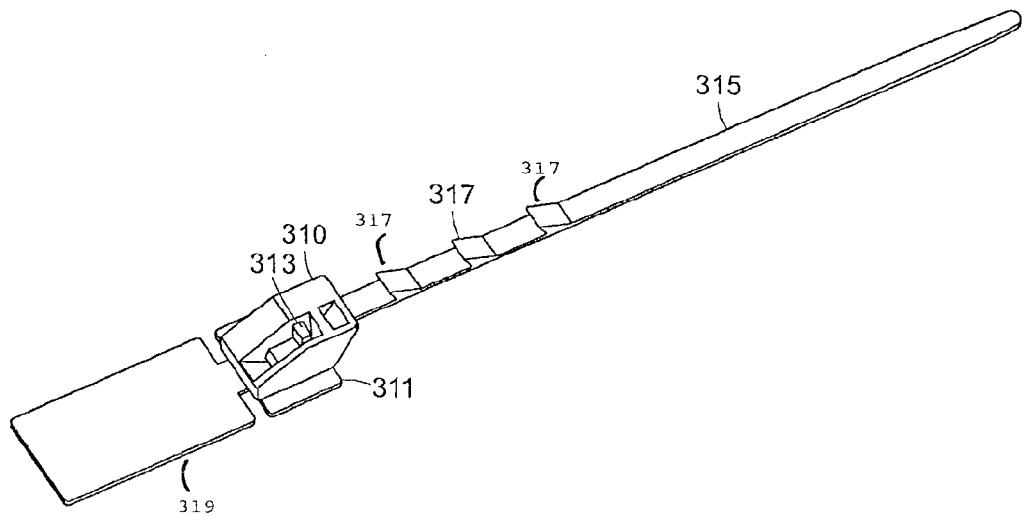
Figure 36:
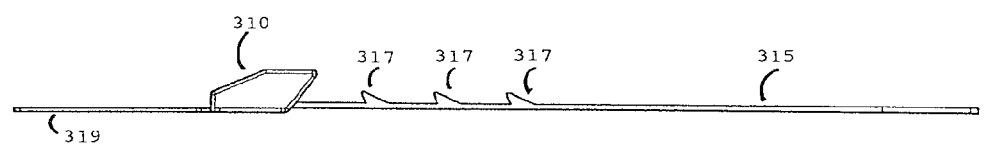
Figure 37:
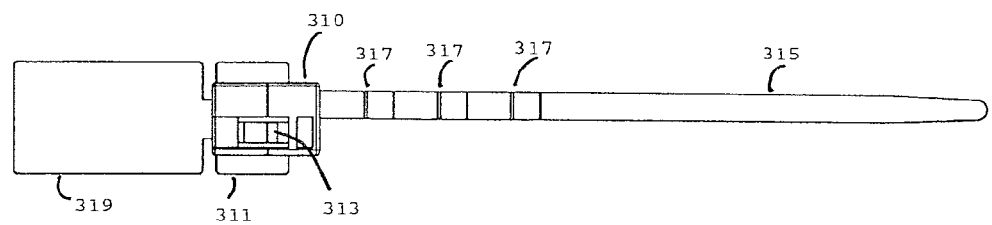
Figure 38:
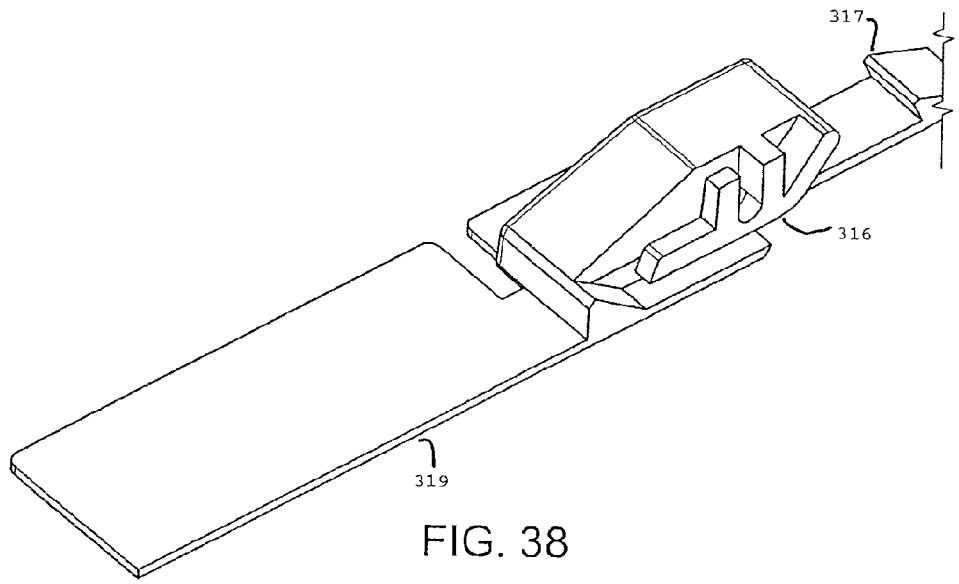
Figure 39:
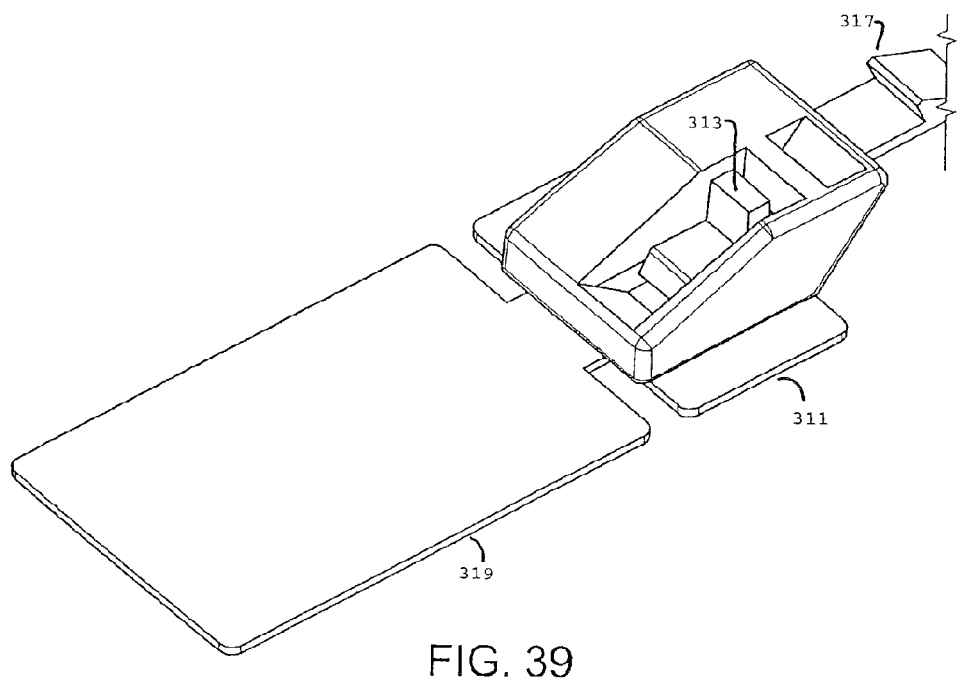
Figure 40:
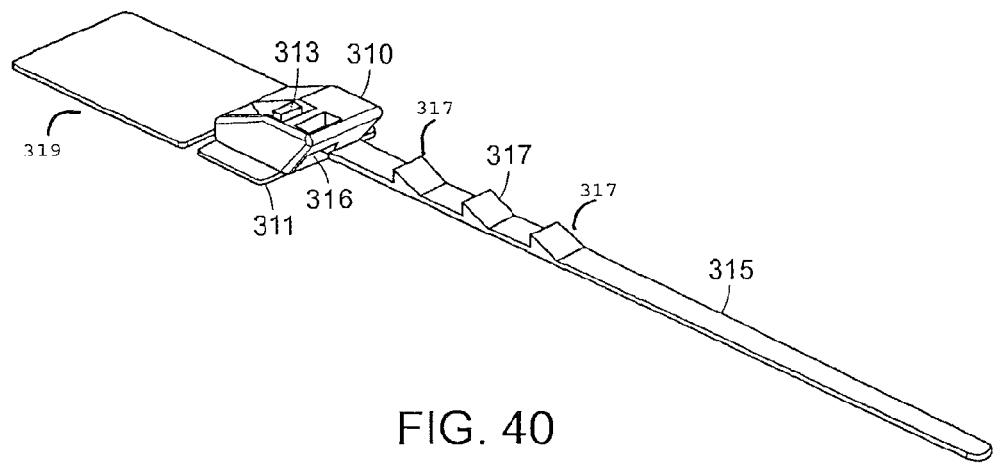

FIGS. 31 through 41 illustrate another embodiment of the invention, the closure component of which has two members. The embodiments illustrated in these figures show variations in the structure of the members. FIGS. 31 and 32, for example, are very similar to the embodiment of FIGS. 31-34. The embodiment of FIGS. 35-41 additionally have flares 311 that extend from bases 310 to provide a larger surface for skin adhesion. Each set of members, as illustrated mated in FIGS. 31-34 and unmated in FIGS. 35-40, is made up of two members, each comprising a base 310, flare 311, and a pull-tab 315. Referring to FIG. 40, base 310 also includes female connective element 316. When the two members are engaged, pull-tab 315 of each member passes through female connective element 316 of the other member. Pull-tab 315 has teeth 317 rising from an upper surface of pull-tab 315. Upon entry of pull-tab 315 into female connective element 316, as each tooth 317 passes through female connective element 316, female connective element 316 locks each tooth 317 into base 310. As seen in FIGS. 35 and 40, base 310 also includes dedicated unlocking hole 313, which is preferably a ratchet locking mechanism. Dedicated unlocking hole 313 can be unlocked using forceps or a needle-like tool to apply pressure to release the ratchet locking mechanism. When pull-tab 315 of each member is pulled through female connective element 316 of each other member, the members are aligned and joined into mated components. Adhesive backing is placed on an underside of base 310, including flares 311, of both pieces. Pieces can be packaged as singles (a single unmated member), single paired (two members mated to each other), multiple singles (multiple unmated members), and multiple paired (multiple mated members).

Referring to FIGS. 31 through 34, pull-tab 315 of each base member 310 is inserted into female connective element 316 of each other base member. Each tooth 317 that enters the female connective element 316 locks into place. As pull-tabs 315 are pulled through female connective element 316 of the other base member 310, bases members 310 move closer to each other. Upon sufficient pulling, base members 310 contact each other at edge 324. Upon continued pulling of pull-tabs 315, surfaces 322 of each base member 310 pivot about edge 324 and move closer to each other. When pull-tabs 315 are pulled sufficiently, surfaces 322 of each base member 310 are substantially contacting each other, as shown in the top portions of FIGS. 31 and 32. When this occurs, the edges between the undersurfaces 320 of each base member 310, which have adhesive covering and which are adhered to the skin during use, and the surface vertical to the base are lifted, causing a skin edge to be everted, thus causing upward traction of the edge of the wound and creating local edge eversion. To facilitate wound edge eversion, the tissue closure devices illustrated in these figures preferably have pull tabs 315 in the lower one third of the height of each member, and preferably have edges 324 in the top one third of the height of each member.

Figure 41B:
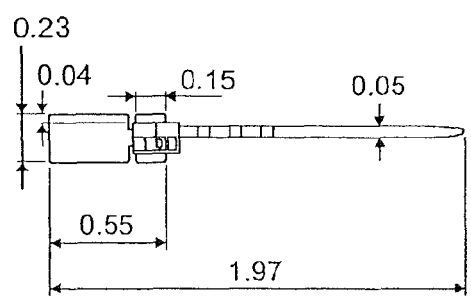
Figure 41A:
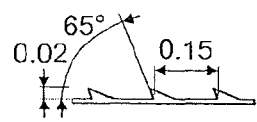
Figure 41:
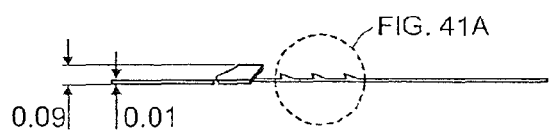

FIG. 41 shows preferred angles and measurements, in centimeters, of base 310, flares 311, teeth 317, and pull-tab 315. The height of the tab base is preferably in the range of approximately 0.005 cm to approximately 0.05 cm, and in a preferred embodiment is approximately 0.01 cm. The height of base 310, which includes the locking mechanism, is preferably in the range of 0.04 cm to 0.2 cm, and in a preferred embodiment is 0.09 cm. The width of flares 311 of the base is preferably in the range of approximately 0.1 cm to approximately 0.5 cm, and in a preferred embodiment is approximately 0.23 cm. The width of flares 311 that extend from base 310 is preferably in the range of approximately 0.005 cm to 0.1 cm, and in a preferred embodiment is 0.04 cm. The length of flare 311 in the direction of tab 315 is preferably in the range of approximately 0.1 cm to approximately 0.5 cm, and in a preferred embodiment is approximately 0.15 cm. The length of base 319 in the direction of the tab is preferably in the range of approximately 0.1 cm to approximately 0.5 cm, and in a preferred embodiment is approximately 0.55 cm. The length of the entire tab, including any optional base 319, is preferably in the range of approximately 0.5 cm to approximately 5.0 cm, and in a preferred embodiment is approximately 1.97 cm. The width of the portion of pull-tab 315 from which teeth 317 protrude is preferably in the range of approximately 0.01 cm to approximately 0.1 cm, and in a preferred embodiment is approximately 0.05 cm. The vertical height of teeth 317 above the base of pull-tab 315 is preferably in the range of approximately 0.005 cm to approximately 0.1 cm, and in a preferred embodiment is approximately 0.02 cm. The distance between base 310 and the tooth 317 closest to the base 310 is preferably in the range of approximately 0.005 cm to approximately 0.2 cm, and in a preferred embodiment is approximately 0.025 cm. Referring to FIG. 41A, the angle between the trailing edge of tooth 317 and an upper plane of tab 315 is preferably in the range of approximately 30 degrees to approximately 90 degrees, and in a preferred embodiment is approximately 65 degrees. Also referring to FIG. 41A, the angle of the leading edge of teeth 317 to an upper plane of tab 315 is preferably in the range of approximately 90 degrees to approximately 180 degrees, and in a preferred embodiment is approximately 150 degrees. The distance between tabs 315 is preferably in the range of approximately 0.005 cm to approximately 0.1 cm, and in a preferred embodiment is approximately 0.15 cm. The total number of teeth 317 per tab is preferably in the range of approximately 1 to approximately 20.

FIGS. 35-41 are additionally shown with optional base 319. Base 319 provides an additional adhesive surface for adhering to the surface of the skin in order to facilitate healing of a wound.

In some embodiments, pull-tab 315 of each base member 310 contains three teeth. In some aspects, the third tooth, which is the tooth farthest from female connective element 316 of the member, has a height that is greater than the height of the other two teeth on pull-tab 315. In such aspects, as the first two teeth on pull-tab 315 of one member are inserted through female connective element 316 of a paired member, they provide tactile feel to the user for the connection of the members. The first two teeth of the one member engage the locking mechanism of female connective element 316 of the paired member. The third tooth, because it has a height greater than the height of the first two teeth, creates a larger interference with the locking mechanism, and thus requires more force for it to pass through female connective element 316 of the paired member. Each tooth, as it passes through the locking mechanism, locks the two members together. As each tooth passes through the locking mechanism, the friction between the tooth and the locking mechanism provides tactile feedback to the person engaging the members. The third tooth, because it is higher than the other teeth, provides increased tactile feedback as compared to the other teeth. The third tooth also engages with the locking mechanism such that it requires more force to disengage the members when the third tooth is locked in the locking mechanism than when the other teeth are engaged in the locking mechanism. Thus it is easier to release the locking mechanism when the other teeth are engaged than it is to release the locking mechanism when the third tooth is engaged.

In other embodiments, each pull-tab 315 of each base member 310 contains more than three teeth, and in some aspects approximately 30 teeth.

In other aspects, each of the alignment members has a locking mechanism. In some aspects, the first member and the second member are identical. In some aspects, the alignment members comprise at least one of a ball and socket mechanism, a ball and slot mechanism, a ratchet mechanism, a suture ligature, magnets, a photobonded mechanism, a staple, and a lock and key mechanism. In some aspects, the alignment members are ratchet mechanisms including a plurality of teeth. In some aspects, the first and second members are releasably coupled and in some aspects the plurality of teeth are non-uniform in height. In some aspects, each alignment member of each closure component has three teeth, and wherein the tooth on each said member furthest from the second surface of each said member has a height greater than the other two teeth on each said member. In other aspects, the members further comprise a second adhesive. In further aspects, the alignment members are positioned substantially in a lower one third portion of the at least first and second members with respect to the height dimension of the at least first and second members. In some aspects, the vertical height of the teeth is in the range of approximately 0.005 cm to approximately 0.1 cm. In other aspects, the teeth of each alignment member are positioned closer to the second surface of that member than to the end of the alignment member as measured along a principle axis of the alignment member. In yet other aspects, the locking mechanism comprises a hollow section for engagement of the teeth.

Care after the closure procedure can be critical to wound healing outcome. For post-procedural care, a wound dressing system can be used. In some embodiments, dressings may be clearly labeled for use with reference to a specific time or period, such as, for example, time from initial injury or period of wound healing. A simple to follow regimen of dressing changes may be performed by the patient. By way of non-limiting example, within the first two days, as an initial skin covering forms, contemplated aspects of the dressing include moisture sealing and pain relief. During subsequent days of normal healing, as support below the skin is normally laid down, in some embodiments, contemplated aspects of the dressing include moisture sealing, infection sensing through pH, exudates reaction, or other factors, and transparency for ease of inspection. During later days of normal healing, as the wound matures, in various embodiments, contemplated aspects of the dressing include vitamin E and other scar reducing compounds.

In various embodiments, the invention provides for a system for promoting wound healing after wound closure having a set of different dressings targeted to time-defined periods of wound healing and a series of patient controlled steps to care for the wound, including placement of specific dressings at specified times. In some embodiments, the dressings are targeted to times corresponding to the physiologic phases of wound healing. In other embodiments, one or more of the dressings is moisture impermeable for use when a moist environment promotes healing. In further embodiments, one or more of the dressings is transparent to allow visualization of a potential infection. In additional embodiments, one or more of the dressings contain a chemical indicator triggered by physiologic changes associated with infection. In some embodiments, the indicator reacts to specific pH levels or protein exudates. In further embodiments, one or more of the dressings releases vitamin E to reduce scarring. In some embodiments, the patient is given a compound or compounds to regularly apply to the dressing to reduce scarring. In additional embodiments, one or more of the dressings releases a chemical solvent leading to easy removal of an adherent wound closure device.

In a preferred embodiment, the invention is applied as follows. Assembly of pairs of members is done prior to packaging and before the user receives the members. Assembly is done by pushing the pull tabs or alignment members through the bottom slots, or connective openings, to initiate alignment and join the paired components. Adhesive backing is applied to both members such that the anterior component is flush with the anterior adhesive backing. Alternatively, the user can assemble pairs of members. An assembly of an embodiment can be a single member, two paired members, multiple non-paired members attached to each other, and multiple sets of paired members.

After the paired members are assembled, the user removes the adhesive backing from one member of a pair of members, or, in the case of multiple sets of paired members, from all members on one side of the attached sets. The user then places the member or members with the adhesive backing removed on cleansed and dry skin so that the anterior face is abutting one edge of the tissue opening. The user then slowly ratchets the paired components, one member of each pair attached to the skin on one side of the wound and the other member of each pair not yet attached to the skin. The user ratchets the paired connections until the second unit of each paired component is placed abutting an opposite skin edge. The user then removes the adhesive backing from the second member or members and places the second member or members near the wound edge. The adhesive is designed such that the user has some time to make minor placement adjustments before the adhesive adheres to the skin surface. This time can range from approximately ten seconds to approximately three minutes, and in a preferred embodiment is approximately one minute. After this time elapses, the user gently pulls the wound edges toward each other by pulling on the alignment tabs. The tabs can be made with a break off point, or the user can cut them after closing the members to the desired range. The user can further unlock the members by placing tool, forceps for example, in the dedicated unlocking hole and applying pressure to release the ratchet locking mechanism.

Depending on the type of adhesive used, the members will naturally exfoliate within approximately seven to ten days. Alternatively, a user can apply a solvent to the adhesive for more immediate removal. The paired members can further be unratcheted a variable distance, for example from approximately 1 mm to approximately 10 mm to allow for drainage of fluids. The paired members can later be re-ratcheted as described above to re-close the wound.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer components may be used in the diagrams.

Other aspects, modifications, and embodiments are within the scope of the following claims.

What is claimed is:

1. A method of non-invasively closing a tissue opening, the method comprising:
    affixing to the skin an assembled pair of substantially identical closure components so that the assembled pair is affixed to the skin in a manner so that each of the closure components is disposed on an opposite side of the tissue opening, each component having:
        a strip with a preapplied adhesive layer on a first side thereof to affix the attachment strip to the skin;
        an assembly mounted on a second side of the strip;
        a toothed pull-tab coupled to the strip through the assembly and defining a longitudinal axis, the assembly having a forward face to which the pull-tab is affixed and an opposed rearward face, the forward face including a sloped portion that is sloped rearward as it approaches the strip; and
        a female connective element mounted on the second side of the strip and built into the assembly for receiving and releasably engaging a pull-tab from the other component and into which the pull-tab from the other component has been placed,
        wherein each pull tab has a length sufficient to reach and be received by the female connective element of the other closure component; and
    drawing the pull tab of each closure component through the female connective element of the other component, so as to close the opening non-invasively while causing substantial contact of the sloped portions of the forward faces of the components with one another and reliably introducing eversion of tissue edges that defined the opening, when each assembly pivots about a location of contact of each forward face thus causing lifting of the forward faces resulting in upward traction of the tissue edges.

2. The method according to claim 1, wherein each strip is porous.

3. The method according to claim 1, wherein the pull tab is coupled to the assembly at a location within the lower one-third of the height of the assembly from the strip.

4. The method according to claim 1, wherein the forward face defines an edge at a location within the upper one third of the height of the assembly from the strip.

5. The method according to claim 1, wherein the strip includes at least one notch, disposed in a direction transverse to the longitudinal axis, and located adjacent to the rearward face of the assembly.

6. The method according to claim 1, further comprising a package in which the assembled pair of components has been placed and stored for use.

7. The method according to claim 1, wherein each pull tab has a plurality of teeth, the teeth non-uniform in height.

8. The method according to claim 1, wherein a tooth farthest from its associated assembly has a height that is greater than the other teeth on the pull tab.

9. The method according to claim 1, wherein each pull tab has three teeth.

* * * * *